US012670777B2

(12) United States Patent
Osuga et al.

(10) Patent No.: US 12,670,777 B2
(45) Date of Patent: Jun. 30, 2026

(54) INFORMATION PROCESSING APPARATUS, INFORMATION PROCESSING METHOD, NON-TRANSITORY COMPUTER-READABLE STORAGE MEDIUM WITH EXECUTABLE INFORMATION PROCESSING PROGRAM STORED THEREON, AND INFORMATION PROCESSING SYSTEM

(71) Applicant: Nintendo Co., Ltd., Kyoto (JP)

(72) Inventors: Seiya Osuga, Kyoto (JP); Junichi Takatori, Kyoto (JP); Sadayoshi Hattori, Kyoto (JP); Shumpei Yamakawa, Kyoto (JP); Yuki Matsuda, Kyoto (JP); Masahiro Kondo, Kyoto (JP)

(73) Assignee: Nintendo Co., Ltd., Kyoto (JP)

( * ) Notice: Subject to any disclaimer, the term of this patent is extended or adjusted under 35 U.S.C. 154(b) by 0 days.

(21) Appl. No.: 18/663,259

(22) Filed: May 14, 2024

(65) Prior Publication Data

US 2024/0296729 A1 Sep. 5, 2024

Related U.S. Application Data

(63) Continuation of application No. 17/355,919, filed on Jun. 23, 2021, now Pat. No. 12,020,552, which is a
(Continued)

(30) Foreign Application Priority Data

Dec. 28, 2018 (JP) ................................. 2018-248120

(51) Int. Cl.
 *G08B 21/06* (2006.01)
 *A61B 5/00* (2006.01)
 (Continued)

(52) U.S. Cl.
 CPC ............ *G08B 21/06* (2013.01); *A61B 5/4809* (2013.01); *A61B 5/4812* (2013.01); *A61M 21/02* (2013.01);
 (Continued)

(58) Field of Classification Search
 CPC ..... G08B 21/06; A61B 5/4809; A61B 5/4812; A61B 5/16; A61B 5/11; A61M 21/02;
 (Continued)

(56) References Cited

U.S. PATENT DOCUMENTS 6,498,600 B1 12/2002 Vance et al.
7,394,451 B1 7/2008 Patten
(Continued)

FOREIGN PATENT DOCUMENTS

JP 3-115890 A 5/1991
JP 4-269690 A 9/1992
(Continued)

OTHER PUBLICATIONS

International Search Report for PCT/IB2019/061352 dated Mar. 17, 2020, 9 pages with English Translation.
(Continued)

*Primary Examiner* — Brian Wilson
(74) *Attorney, Agent, or Firm* — Nixon & Vanderhye P.C.

(57) ABSTRACT

A new configuration capable of performing processing in accordance with a sleep state of a user and at least one of a position and motion of the user is provided. An information processing apparatus includes a sensing unit that outputs a signal depending on motion of the user, a sleep state measurement unit that measures the sleep state of the user based on an output from the sensing unit, a user state measurement unit that measures a user state representing at least one of the position and the motion of the user based on the output from the sensing unit, and a processing perform-
(Continued)

MEASUREMENT
2  22
INCIDENT WAVE
REFLECTED WAVE
21

BD ing unit that performs prescribed processing based on at least one of the sleep state of the user measured by the sleep state measurement unit and the user state measured by the user state measurement unit.

20 Claims, 17 Drawing Sheets

Related U.S. Application Data continuation of application No. PCT/IB2019/061352, filed on Dec. 25, 2019.

(51) Int. Cl.
  *A61M 21/02*          (2006.01)
  *A61M 21/00*          (2006.01)
(52) U.S. Cl.
  CPC . *A61M 2021/0083* (2013.01); *A61M 2230/63* (2013.01)
(58) Field of Classification Search
  CPC ...... A61M 2021/0083; A61M 2230/63; A61M 2021/0027; A61M 2205/18
  See application file for complete search history.

(56)                    References Cited

U.S. PATENT DOCUMENTS

| | | | |
|---|---|---|---|
| 2003/0095476 A1 | 5/2003 | Mollicone et al. | |
| 2004/0210155 A1* | 10/2004 | Takemura | A61B 5/00 |
| | | | 702/159 |
| 2005/0248962 A1* | 11/2005 | Searfoss | A61M 21/02 |
| | | | 362/642 |
| 2013/0114382 A1 | 5/2013 | Xu | |
| 2014/0276119 A1 | 9/2014 | Venkatraman et al. | |
| 2016/0005290 A1 | 1/2016 | Takahashi | |
| 2016/0005291 A1 | 1/2016 | Takahashi | |
| 2016/0151603 A1* | 6/2016 | Shouldice | G16H 20/70 |
| | | | 600/26 |

| | | | |
|---|---|---|---|
| 2017/0045862 A1 | 2/2017 | Jia | |
| 2017/0182284 A1 | 6/2017 | Ueya et al. | |
| 2020/0160797 A1* | 5/2020 | Zeinstra | G09G 3/36 |
| 2021/0150873 A1 | 5/2021 | Shouldice | |

FOREIGN PATENT DOCUMENTS

| | | | |
|---|---|---|---|
| JP | 5-87960 | A | 4/1993 |
| JP | 6-27269 | | 1/1994 |
| JP | 2002-372593 | A | 12/2002 |
| JP | 2008-222 | A | 1/2008 |
| JP | 2009-85901 | A | 4/2009 |
| JP | 2009-232925 | A | 10/2009 |
| JP | 2011-109432 | A | 6/2011 |
| JP | 2012-132857 | A | 7/2012 |
| JP | 2013-213642 | | 10/2013 |
| JP | 2014-14708 | | 1/2014 |
| JP | 2014-509734 | A | 4/2014 |
| JP | 2015-215194 | A | 12/2015 |
| JP | 2016-13221 | A | 1/2016 |
| JP | 2016-14542 | A | 1/2016 |
| JP | 2016-24165 | A | 2/2016 |
| JP | 2016-532481 | A | 10/2016 |
| JP | 2017-113263 | | 6/2017 |
| JP | 2017-169933 | | 9/2017 |
| JP | 2018-149076 | | 9/2018 |
| WO | 2015/006364 | | 1/2015 |

OTHER PUBLICATIONS

"Vantage Installation TouchP Int LCD320C5" (Vantage Controls 2003).

Decision to Grant a Patent issued in JP Application No. 2020-561978 dated Nov. 14, 2023.

PIR Pyroelectric Infrared Sensor Model No. PIS01E Waitrony (Rev. 1-00-05-27), 1998.

Communication dated Jul. 23, 2024 in JP counterpart application (see global dossier).

Communication dated Mar. 25, 2025 in JP counterpart application (see global dossier).

* cited by examiner

INFORMATION PROCESSING APPARATUS, INFORMATION PROCESSING METHOD, NON-TRANSITORY COMPUTER-READABLE STORAGE MEDIUM WITH EXECUTABLE INFORMATION PROCESSING PROGRAM STORED THEREON, AND INFORMATION PROCESSING SYSTEM

This application is a continuation of application Ser. No. 17/355,919 filed on Jun. 23, 2021, now U.S. Pat. No. 12,020,552, which is a continuation of International Application No. PCT/IB2019/061352 filed on Dec. 25, 2019, which claims priority to Japanese Application No. 2018-248120 filed on Dec. 28, 2018, the entire contents of each of which are hereby incorporated by reference herein.

FIELD

The present disclosure relates to a method of measuring a sleep state of a user.

BACKGROUND AND SUMMARY

A technique for processing a biological signal such as breath, heartbeat, and body motion of a user to determine depth of sleep of a living body has conventionally been proposed.

According to the conventional technique, body motion or depth of sleep of a user is measured and processing making use of a result of measurement is simply performed. The conventional technique has paid no attention to a position or motion of the user. An object of the present disclosure is to provide a new configuration capable of performing processing in accordance with a sleep state of a user or a position or motion of the user.

An information processing apparatus according to one embodiment includes a sensing unit that outputs a signal depending on motion of a user, a sleep state measurement unit that measures a sleep state of the user based on an output from the sensing unit, a user state measurement unit that measures a user state representing at least one of a position and motion of the user based on the output from the sensing unit, and a processing performing unit that performs prescribed processing based on at least one of the sleep state of the user measured by the sleep state measurement unit and the user state measured by the user state measurement unit.

According to the present configuration, processing suitable for a user can be performed based on at least one of the sleep state of the user measured by the sleep state measurement unit and the user state measured by the user state measurement unit.

The sensing unit may include a Doppler sensor. The sleep state measurement unit may measure the sleep state of the user based on an output from the Doppler sensor, and the user state measurement unit may measure the user state based on the output from the Doppler sensor. According to the present configuration, an identical Doppler sensor can be used to measure both of the sleep state of the user and the user state.

The sleep state measurement unit and the user state measurement unit may conduct measurement in parallel in response to the output from the sensing unit. According to the present configuration, results of measurement of the sleep state and the user state can be obtained in parallel. Therefore, processing can be performed in real time.

The user state may include information on whether the user is moving or non-moving. According to the present configuration, a state such as whether or not the user is sufficiently awake can be measured, for example, based on the user state.

The user state may include information on whether or not the user is present within a measurable area of the sensing unit. According to the present configuration, whether or not the user is actually present can be measured based on the user state.

The processing performing unit may perform the prescribed processing based on both of the sleep state of the user measured by the sleep state measurement unit and the user state measured by the user state measurement unit. According to the present configuration, more appropriate processing can be performed based on both of the sleep state of the user and the user state.

The prescribed processing may include processing relating to an audio alarm for the user. According to the present configuration, a service relating to the audio alarm such as an alarm for getting up can be provided to the user.

The user state measurement unit may measure as the user state, whether or not the user is present within a user-lying area set as an area where the user will lie during sleep. According to the present configuration, whether or not the user has left the bed can be measured.

When the audio alarm is ringing, in response to the determination that a period for which the user is determined as not being present within the user-lying area is equal to or longer than a first prescribed time period, the processing performing unit may lower a volume of the audio alarm, as the prescribed processing. According to the present configuration, when it is highly likely that the user has left the bed, the volume of the audio alarm is automatically lowered.

When the audio alarm is ringing, in response to the determination that a period for which the user is determined as not being present within the user-lying area is equal to or longer than a second prescribed time period, the processing performing unit may stop the audio alarm, as the prescribed processing. According to the present configuration, when the user is determined as having left the bed, the audio alarm is automatically stopped.

The prescribed processing may include processing for activating the audio alarm when time set in advance comes. In response to the determination that the user is determined as not being present within the user-lying area at the time when the time set in advance comes, the processing performing unit may provide a first voice message instead of the audio alarm. According to the present configuration, a wake-up alarm function or the like can be provided.

The information processing apparatus may further include a body motion sensing unit that senses body motion of the user based on the output from the sensing unit. According to the present configuration, whether the user is in an active state or a resting state can be measured.

In response to sensing, by the body motion sensing unit, of the body motion of the user after the first voice message is provided, the processing performing unit may postpone activation of the audio alarm. According to the present configuration, activation of the audio alarm can arbitrarily be postponed based on a clear user's intention.

In response to the determination that the body motion sensing unit does not sense the body motion of the user during a stand-by time period after the first voice message is provided, the processing performing unit may quit performing the prescribed processing. According to the present configuration, when the user has left the bed or is absent, unnecessary activation of the audio alarm can be avoided.

The prescribed processing may include processing for activating the audio alarm when time set in advance comes. In response to determining, by the sleep state measurement unit, that the user has gotten up at the time when the time set in advance comes, the processing performing unit may provide a second voice message instead of the audio alarm. According to the present configuration, a voice message suitable for the user who has already gotten up can be provided to the user who has gotten up, rather than the audio alarm for getting up.

In response to sensing, by the body motion sensing unit, of the body motion of the user after the second voice message is provided, the processing performing unit may quit processing for activating the audio alarm. According to the present configuration, when activating the audio alarm can be determined as being unnecessary based on body motion of the user, unnecessary activation of the audio alarm can be avoided.

In response to sensing, by the body motion sensing unit, of no body motion of the user after the second voice message is provided, the processing performing unit may activate the audio alarm. According to the present configuration, when the user is determined as not having gotten up, the audio alarm can be given for getting the user up.

The prescribed processing may include processing for activating the audio alarm in response to the determination that the user has slept for an amount equal to or larger than a predetermined amount. According to the present configuration, without setting time to get up in advance, the user can be caused to get up at the time point when the user can be determined as having sufficiently slept.

The processing performing unit may determine whether or not the user has slept for the amount equal to or larger than the predetermined amount based on a score calculated based on a result of measurement by the sleep state measurement unit. According to the present configuration, the state of sleep of the user can be expressed in a numerical score and the score can objectively be made use of.

An information processing apparatus according to another embodiment includes a sensing unit that outputs a signal depending on motion of a user, a sleep state measurement unit that measures a sleep state of the user based on an output from the sensing unit, and a processing performing unit that performs prescribed real-time processing based on the sleep state successively measured by the sleep state measurement unit.

According to the present configuration, processing in accordance with the sleep state of the user measured by the sleep state measurement unit can be performed in real time.

The sleep state measurement unit may calculate, based on data obtained by accumulation of outputs for at least a measurement period from start of sleep until wake of the user, the sleep state over the measurement period. According to the present configuration, the sleep state can more accurately be measured.

The prescribed real-time processing may relate to control of an alarm. According to the present configuration, such control as giving an alarm in accordance with the sleep state of the user can be carried out in real time.

The prescribed real-time processing may include processing for activating an audio alarm when time set in advance comes. The processing performing unit may perform the real-time processing in response to transition of the sleep state to a prescribed state before the time set in advance. According to the present configuration, processing for activating the audio alarm for getting the user up can be performed in real time.

The real-time processing may be performed to control audio output. According to the present configuration, output of sound appropriate for the user can be provided in accordance with the sleep state or the like of the user.

The information processing apparatus may further include a user state measurement unit that measures a user state representing at least one of a position and motion of the user based on the output from the sensing unit. The sleep state measurement unit and the user state measurement unit may conduct measurement in parallel in response to the output from the sensing unit. According to the present configuration, processing in accordance with results of measurement of both of the sleep state and the user state can be performed in real time.

The user state may represent presence or absence of the user. According to the present configuration, whether or not the user is actually present can be measured based on the user state.

The user state may represent that the user is moving or non-moving. According to the present configuration, for example, a state such as whether or not the user is sufficiently awake can be measured based on the user state.

According to yet another embodiment, an information processing method in an information processing apparatus including a sensing unit that outputs a signal depending on motion of a user is provided. The information processing method includes measuring a sleep state of the user based on an output from the sensing unit, measuring a user state representing at least one of a position and motion of the user based on the output from the sensing unit, and performing prescribed processing based on at least one of the measured sleep state of the user and the measured user state.

According to the present configuration, processing suitable for a user can be performed based on at least one of the sleep state of the user measured by a sleep state measurement unit and the user state measured by a user state measurement unit.

According to still another embodiment, an information processing program executed by a computer including a sensing unit that outputs a signal depending on motion of a user is provided. The information processing program causes the computer to perform measuring a sleep state of the user based on an output from the sensing unit, measuring a user state representing at least one of a position and motion of the user based on the output from the sensing unit, and performing prescribed processing based on at least one of the measured sleep state of the user and the measured user state.

According to the present configuration, processing suitable for a user can be performed based on at least one of the sleep state of the user measured by a sleep state measurement unit and the user state measured by a user state measurement unit.

An information processing system according to still another embodiment includes a sensing device that outputs a signal depending on motion of a user and a control device. The control device includes a sleep state measurement unit that measures a sleep state of the user based on an output from the sensing device, a user state measurement unit that measures a user state representing at least one of a position and motion of the user based on the output from the sensing device, and a processing performing unit that performs prescribed processing based on at least one of the sleep state of the user measured by the sleep state measurement unit and the user state measured by the user state measurement unit.

According to the present disclosure, a new configuration capable of performing processing in accordance with a sleep state of a user and a position or motion of the user can be provided.

DETAILED DESCRIPTION OF NON-LIMITING EXAMPLE EMBODIMENTS

Figure 1:
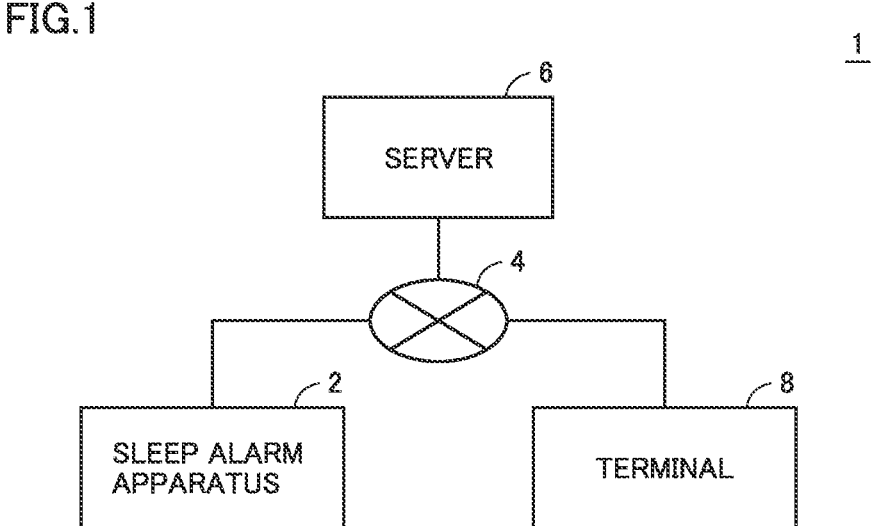
FIG. 1 is a schematic block diagram showing a basic configuration of a sleep management system according to the present embodiment.

The present embodiment will be described in detail with reference to the drawings. The same or corresponding elements in the drawings have the same reference characters allotted and description thereof will not be repeated.

An information processing apparatus in the present embodiment will be described as a sleep alarm apparatus by way of example. A portable (also referred to as mobile) apparatus or a stationary apparatus may be applicable.

A. Configuration of Sleep Management System

An exemplary configuration of the entire sleep management system 1 and each apparatus according to the present embodiment will initially briefly be described.
(a1: Sleep Management System 1)
FIG. 1 is a schematic block diagram showing a basic configuration of sleep management system 1 according to the present embodiment. Referring to FIG. 1, sleep management system 1 includes a sleep alarm apparatus 2, a server 6, and a terminal 8 that are connected to one another over a network 4.

Information can be transmitted and received among sleep alarm apparatus 2, server 6, and terminal 8 over network 4. Network 4 may adopt any of wireless communication and wired communication.

Sleep alarm apparatus 2 manages sleep of a user. Sleep alarm apparatus 2 performs an alarm function to wake the user up and a sensor function to contactlessly sense a signal depending on motion of the user. When a notification condition is satisfied, sleep alarm apparatus 2 performs a notification operation by output of alarm sound from a speaker or the like which represents an exemplary notification unit, and when a notification stop condition is satisfied, it stops output of alarm sound.

Sleep data obtained by sleep alarm apparatus 2 is stored in server 6.

Figure 2:
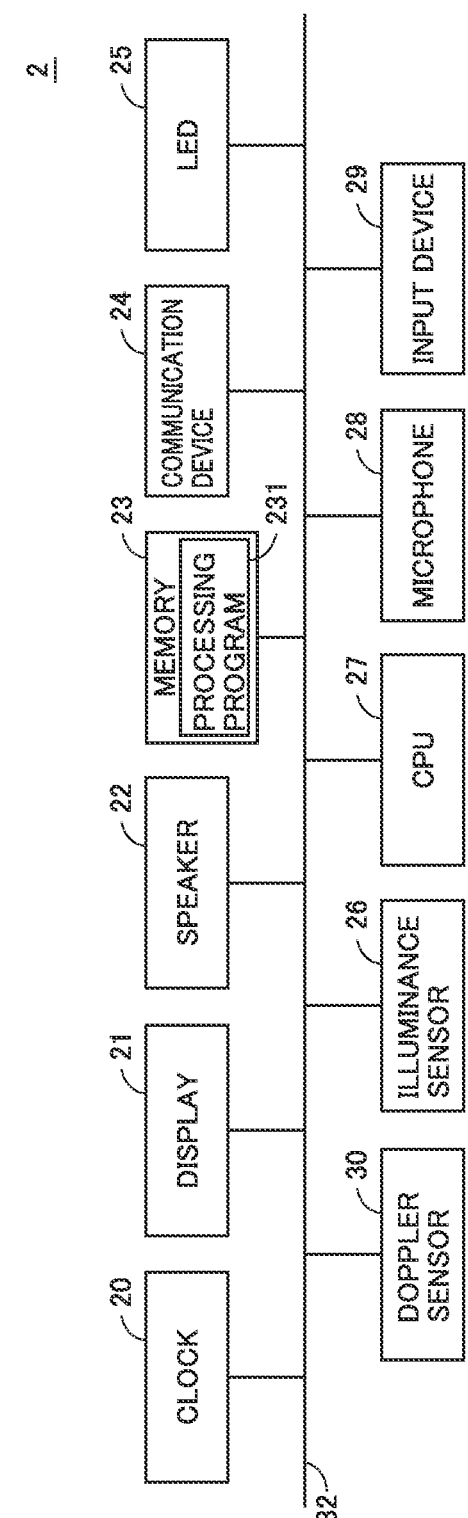
FIG. 2 is a schematic block diagram showing a basic configuration of a sleep alarm apparatus according to the present embodiment.

Terminal 8 obtains setting for the alarm function of sleep alarm apparatus 2 and information on a sleep state of the user and shows them. Terminal 8 may be a portable (also referred to as mobile) apparatus such as a portable telephone or a smartphone or a stationary apparatus such as a personal computer.
(a2: Sleep Alarm Apparatus 2)
FIG. 2 is a schematic block diagram showing a basic configuration of sleep alarm apparatus 2 according to the present embodiment. Referring to FIG. 2, sleep alarm apparatus 2 includes a clock 20, a display 21, a speaker 22, a memory 23, a communication device 24, an LED 25, an illuminance sensor 26, a CPU 27, a microphone 28, an input device 29, a Doppler sensor 30, and an internal bus 32. Components are connected through internal bus 32.

CPU 27 represents one of processors and corresponds to an information processing unit for implementing various types of information processing performed in sleep alarm apparatus 2. CPU 27 performs various types of information processing by using memory 23.

A processing program 231 executed in sleep alarm apparatus 2 is stored in memory 23. Though FIG. 2 illustrates an example in which memory 23 serves as a storage contained in sleep alarm apparatus 2, for example, a storage medium attachable to and removable from sleep alarm apparatus 2 such as an optical disc or a cartridge may be applicable or both of the storage and the storage medium as such may be applicable.

CPU 27 implements processing and various functional blocks involved with various functions based on processing program 231 stored in memory 23.

Clock 20 performs a function to count time. Display 21 shows information such as time. Speaker 22 provides alarm sound as notification sound. Communication device 24 is an interface for communication with an external apparatus (for example, server 6 and terminal 8) over network 4. LED 25 is turned on in response to an instruction and lights up an area around sleep alarm apparatus 2. Microphone 28 accepts external audio input. Input device 29 includes various operation buttons.

Doppler sensor 30 implements at least a part of a sensing unit, and emits radio waves (microwaves) to a measurement target to output a signal (which is also referred to as a "sensing signal" below) depending on motion of the measurement target (typically, a user).

(a3: Server 6)

Figure 3:
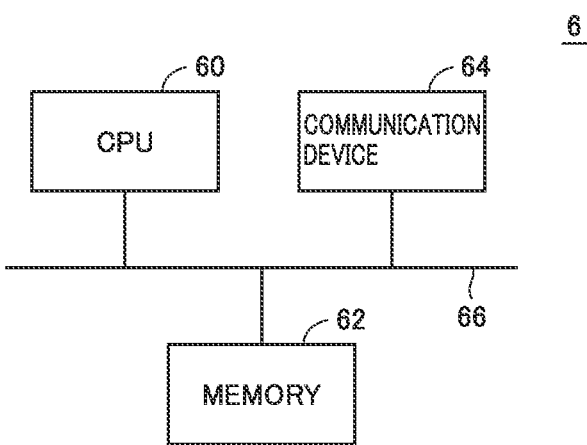
FIG. 3 is a schematic block diagram showing a basic configuration of a server according to the present embodiment.

FIG. 3 is a schematic block diagram showing a basic configuration of server 6 according to the present embodiment. Referring to FIG. 3, server 6 includes a CPU 60, a memory 62, a communication device 64, and an internal bus 66. Components are connected through internal bus 66.

CPU 60 represents one of processors and corresponds to an information processing unit for implementing various types of information processing performed in server 6. CPU 60 performs various types of information processing by using memory 62.

Various programs executed in server 6 and data or the like on sleep measured in real time when the user sleeps are stored in memory 62. Though FIG. 3 illustrates an example in which memory 62 serves as a storage contained in server 6, for example, a storage medium attachable to and removable from server 6 such as an optical disc or a cartridge may be applicable or both of the storage and the storage medium as such may be applicable.

Communication device 64 is an interface for communication with an external apparatus (for example, sleep alarm apparatus 2 and terminal 8) over network 4.

(a4: Terminal 8)

Figure 4:
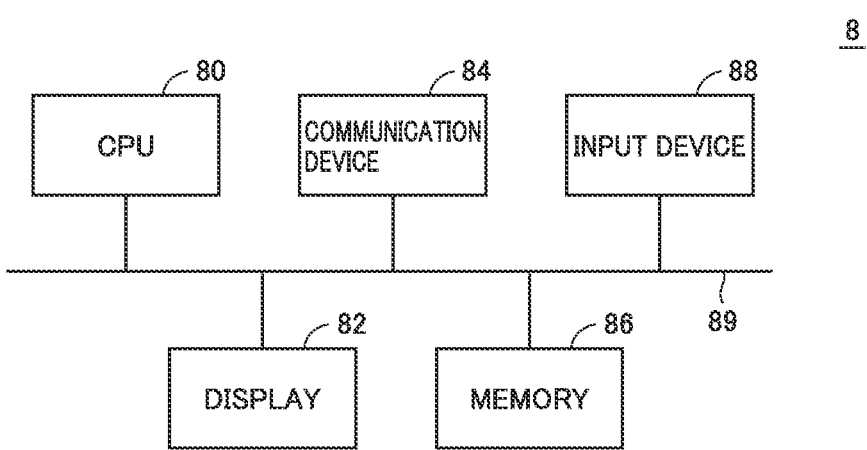
FIG. 4 is a schematic block diagram showing a basic configuration of a terminal according to the present embodiment.

FIG. 4 is a schematic block diagram showing a basic configuration of terminal 8 according to the present embodiment. Referring to FIG. 4, terminal 8 includes a CPU 80, a display 82, a communication device 84, a memory 86, an input device 88, and an internal bus 89. Components are connected through internal bus 89.

CPU 80 represents one of processors and corresponds to an information processing unit for implementing various types of information processing performed in terminal 8. CPU 80 performs various types of information processing by using memory 86.

Various programs executed in terminal 8 are stored in memory 86. Though FIG. 4 illustrates an example in which memory 86 serves as a storage contained in terminal 8, for example, a storage medium attachable to and removable from terminal 8 such as a memory card may be applicable or both of the storage and the storage medium as such may be applicable.

Communication device 84 is an interface for communication with an external apparatus (for example, sleep alarm apparatus 2 and server 6) over network 4.

Input device 88 includes any button, key, touch panel, and the like.

B. Form of Use of Sleep Alarm Apparatus 2

Figure 5:
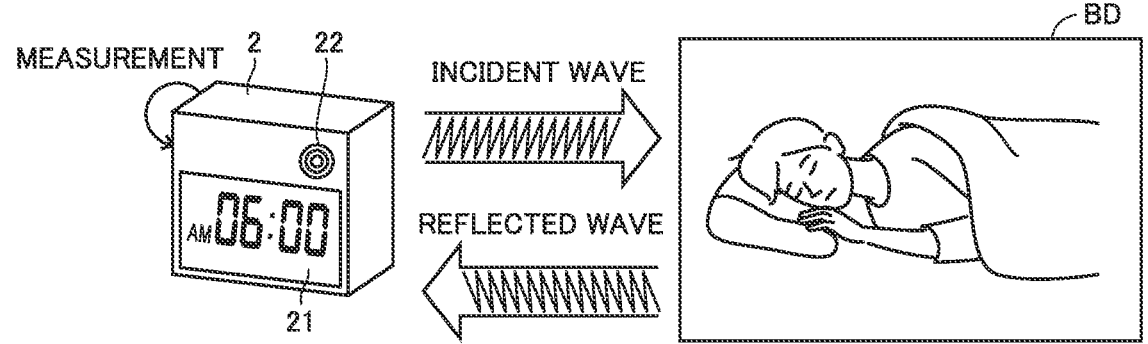
FIG. 5 is a schematic diagram showing an exemplary form of use of the sleep alarm apparatus according to the present embodiment.

One exemplary form of use of sleep alarm apparatus 2 according to the present embodiment will now be described. FIG. 5 is a schematic diagram showing an exemplary form of use of sleep alarm apparatus 2 according to the present embodiment. Referring to FIG. 5, sleep alarm apparatus 2 is arranged adjacently to a bed BD or the like of a user.

Sleep alarm apparatus 2 emits incident waves from Doppler sensor 30 to the user and receives reflected waves that may be produced by reflection of the incident waves at the user. Then, sleep alarm apparatus 2 measures various types of information on the user based on the emitted incident waves and the received reflected waves. A region of observation by sleep alarm apparatus 2 corresponds to a prescribed region (a prescribed area) in bed BD of the user.

Sleep alarm apparatus 2 may perform a clock function and an alarm function. In this case, sleep alarm apparatus 2 may provide alarm sound from speaker 22 when the notification condition is satisfied. On display 21, "AM 6:00" is shown as the current time counted by clock 20, by way of example.

C. Functional Configuration

A functional configuration of sleep alarm apparatus 2 according to the present embodiment will now be described. Sleep alarm apparatus 2 can measure various types of information on a user with Doppler sensor 30.

Various types of information on a user include (1) a distance to the user, (2) magnitude of motion of the user, (3) probability of presence or absence of the user, (4) a sleep state of the user, (5) a position or motion of the user (which is also referred to as a "user state" below), and the like. Various types of processing are performed by making use of such information. All of these pieces of information do not have to be measured, and a function to measure information as appropriate should only be implemented as necessary.

Figure 6:
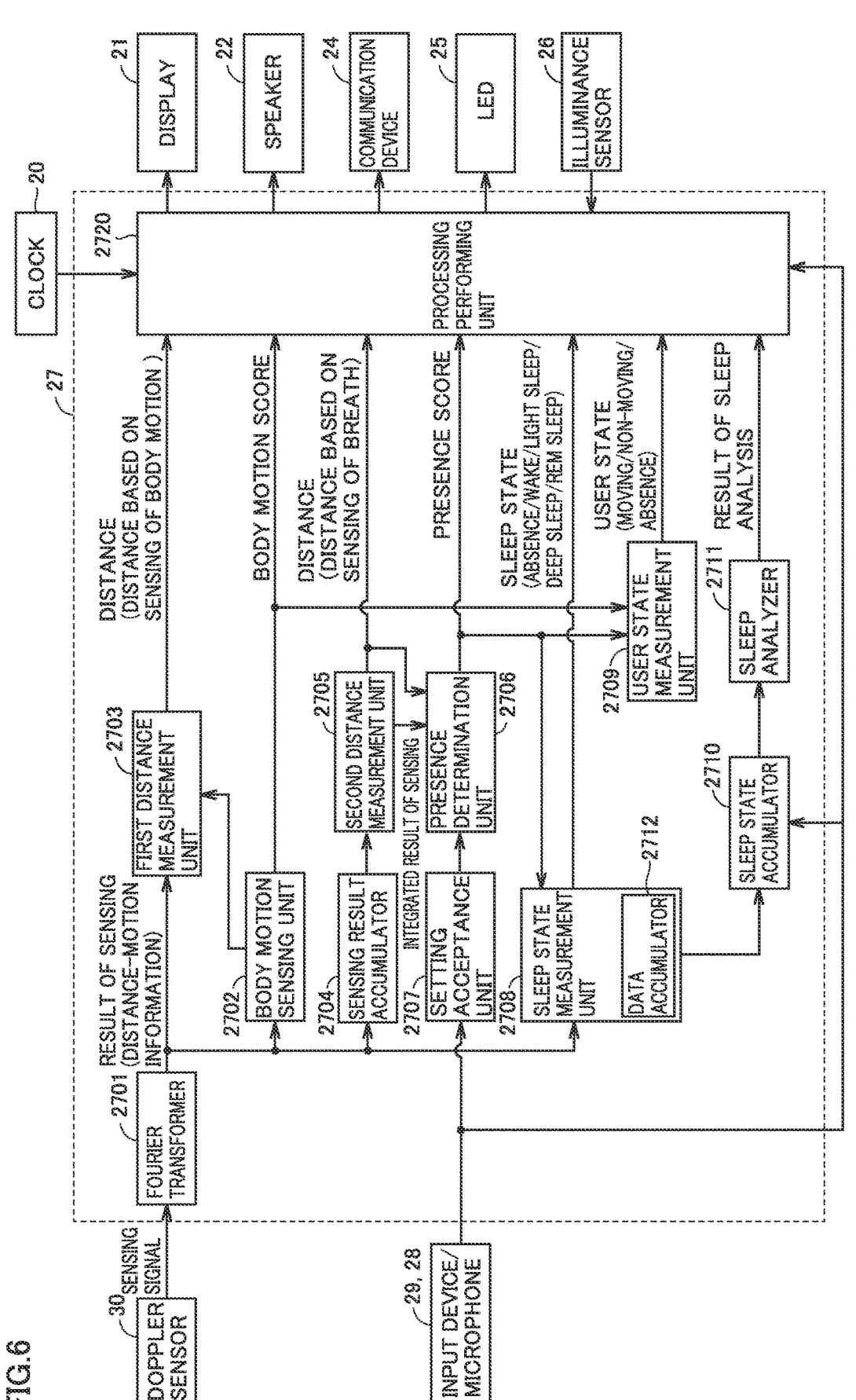
FIG. 6 is a schematic diagram showing an exemplary functional configuration of the sleep alarm apparatus according to the present embodiment.

FIG. 6 is a schematic diagram showing an exemplary functional configuration of sleep alarm apparatus 2 according to the present embodiment. Referring to FIG. 6, sleep alarm apparatus 2 obtains or calculates information necessary for performing various types of processing relating to sleep as will be described later. More specifically, sleep alarm apparatus 2 includes, as its functional configuration, a Fourier transformer 2701, a body motion sensing unit 2702, a first distance measurement unit 2703, a sensing result accumulator 2704, a second distance measurement unit 2705, a presence determination unit 2706, a setting acceptor 2707, a sleep state measurement unit 2708, a user state measurement unit 2709, a sleep state accumulator 2710, a sleep analyzer 2711, and a processing performing unit 2720.

These functions may be implemented by execution of processing program 231 stored or developed in memory 23 by CPU 27 of sleep alarm apparatus 2 in an order set in advance. Each function included in sleep alarm apparatus 2 will be described below in detail.

(c1: Doppler Sensor 30 and Fourier Transformer 2701)

Sleep alarm apparatus 2 according to the present embodiment may be configured to sense in real time with Doppler sensor 30, a distance to a measurement target (typically, a user) present within a measurement area and motion of the measurement target.

Doppler sensor 30 emits incident waves to the measurement target and receives reflected waves that may be produced by reflection of the incident waves at the measurement target. By making use of such a phenomenon that a frequency of the incident waves is varied to a frequency of reflected waves as a result of motion of the measurement target, a signal depending on motion of the user who is the measurement target is provided. A continuous wave (CW) scheme and a frequency modulated continuous wave (FMCW) scheme have been known as schemes for measurement using Doppler sensor 30. Though any scheme may be adopted in the present embodiment, processing under the FMCW scheme will be described as a typical example.

Figures 7A, 7B:
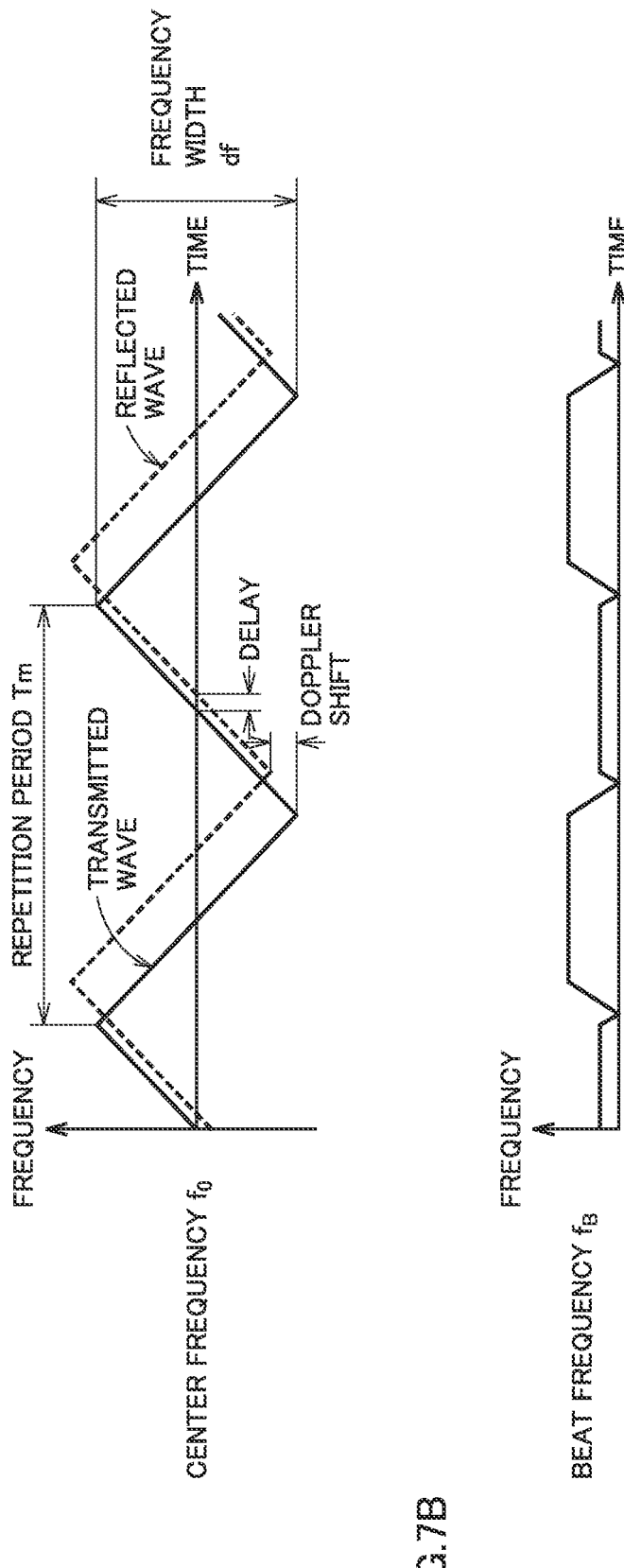
FIGS. 7A and 7B are diagrams for illustrating a scheme for measurement with a Doppler sensor of the sleep alarm apparatus according to the present embodiment.

FIGS. 7A and 7B are diagrams for illustrating a scheme for measurement with Doppler sensor 30 of sleep alarm apparatus 2 according to the present embodiment. Referring to FIG. 7A, a frequency of incident waves emitted from Doppler sensor 30 is repeatedly varied (swept) every prescribed period. FIGS. 7A and 7B show examples of monotonous variation (monotonous increase and monotonous decrease) within a range of a frequency width df every repetition period $T_m$ with a center frequency $f_0$ being defined as the center. In other words, FIGS. 7A and 7B show such a waveform that the frequency is varied like a sawtooth.

By varying such a frequency, a frequency of reflected waves is also varied as following such variation. Magnitude of delay between the incident waves and the reflected waves and magnitude of a frequency difference (Doppler shift) between the incident waves and the reflected waves are varied depending on a distance to the measurement target (that is, a position of the measurement target with Doppler sensor 30 being defined as the reference) and motion.

A mixer within Doppler sensor 30 mixes transmitted waves and reflected waves so that a sensing signal at an intermediate frequency is provided. The provided sensing signal includes as its main component, a beat frequency $f_B$ as shown in FIG. 7B. Beat frequency $f_B$ corresponds to a frequency difference between the transmitted waves and the reflected waves, and reflects a distance to the measurement target and motion of the measurement target. As a result of Fourier transform of a time waveform of the sensing signal mainly composed of beat frequency $f_B$, information representing the distance to the measurement target and magnitude of motion of the measurement target can be obtained.

Figure 8:
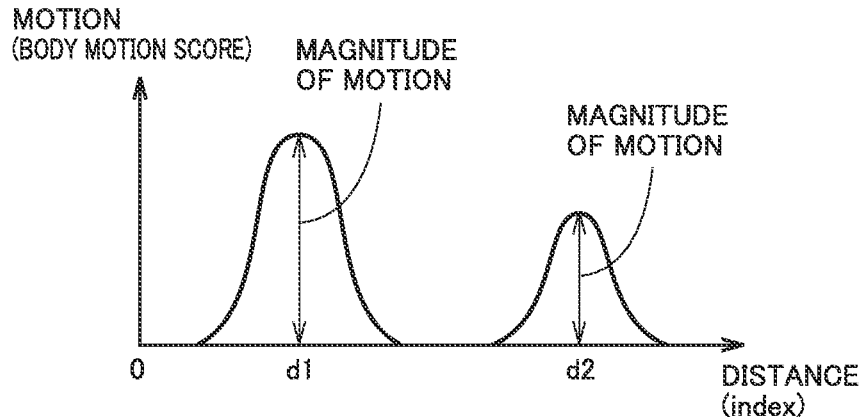
FIG. 8 is a diagram showing an exemplary result of Fourier transform of a sensing signal from the Doppler sensor of the sleep alarm apparatus according to the present embodiment.

FIG. 8 is a diagram showing an exemplary result of Fourier transform of a sensing signal from Doppler sensor 30 of sleep alarm apparatus 2 according to the present embodiment. Referring to FIG. 8, as a result of Fourier transform of the sensing signal from Doppler sensor 30, a result of sensing (distance-motion information) showing relation between the distance and motion can be obtained. More specifically, in a result of Fourier transform shown in FIG. 8, the abscissa represents a distance and the ordinate represents magnitude of motion. Though FIG. 8 continuously shows the distance and magnitude of motion, magnitude of motion may also be defined for each section delimited at every prescribed distance. In the description below, a number that identifies each section may also be called an "index".

In the exemplary result of sensing shown in FIG. 8, two peaks appear; a position of each peak represents the distance and a height of each peak represents magnitude of motion. It can be seen in the example shown in FIG. 8 that the measurement target is present at positions at a distance d1 and a distance d2.

Fourier transformer 2701 subjects sensing signals over a prescribed period from Doppler sensor 30 to Fourier transform. Though any approach can be adopted as a Fourier transform approach, fast Fourier transform (FFT) may typically be adopted. A time waveform obtained in a section where a frequency is increased and a time waveform obtained in a section where a frequency is decreased may be separated to obtain a sensing signal to be subjected to Fourier transform. For example, only a single time waveform or only a set of time waveforms obtained in the section where the frequency is increased in a repetition period shown in FIGS. 7A and 7B may be subjected to Fourier transform, or only a single time waveform or only a set of time waveforms obtained in the section where the frequency is decreased in the repetition period shown in FIGS. 7A and 7B may be subjected to Fourier transform.

The result of Fourier transform (distance-motion information) provided from Fourier transformer 2701 is updated every repetition period or every integer multiple of the repetition period. In the description below, each of results of Fourier transform (distance-motion information) may also be referred to as a "frame".

Fourier transformer 2701 may be incorporated in a part of Doppler sensor 30. Therefore, the sensing unit that outputs a signal depending on motion of the user may be configured with a single Doppler sensor 30 alone or may include both of Doppler sensor 30 and Fourier transformer 2701. Alternatively, a plurality of Doppler sensors 30 may be adopted. (c2: Body Motion Sensing Unit 2702)

Sleep alarm apparatus 2 according to the present embodiment may be able to detect with Doppler sensor 30, relatively large body motion such as turn-over or an operation to wave a hand. Distinction from slight motion due to breath or heartbeat of the user can be made, for example, based on an amount of change between incident waves and reflected waves or periodicity.

Relatively large motion of the user such as turn-over or an operation to wave a hand is herein called "body motion," and such motion, together with slight motion such as breath or heartbeat, may be called "motion".

Sleep alarm apparatus 2 may further be configured to be able to sense magnitude of body motion of the user based on a sensing signal from Doppler sensor 30 depending on motion of the user. In the description below, an indicator that indicates magnitude of body motion of the user may also be referred to as a "body motion score."

The body motion score is an indicator that indicates a probability of occurrence of relatively large motion of a body of the user (an operation to get in the bed or turn-over). In the present embodiment, as the user moves the body to a larger extent, a value of the body motion score is also larger.

Body motion sensing unit 2702 (FIG. 6) senses body motion of the user based on an output from the sensing unit that outputs a signal depending on motion of the user. More specifically, body motion sensing unit 2702 specifies a peak at which magnitude of motion is maximum by referring to a result of Fourier transform (distance-motion information) provided from Fourier transformer 2701 and provides magnitude of motion at the specified peak as magnitude of body motion of the user (a body motion score). For example, the body motion score may be provided as a value normalized to be within a range including a decimal between 0 and 1.

In order to enhance accuracy in sensing, determination as presence of body motion of the user may be made only when magnitude of motion at the specified peak exceeds a threshold value set in advance, and that magnitude may be provided as magnitude of body motion of the user. In other words, when magnitude of motion of the specified peak is equal to or smaller than the threshold value set in advance, body motion of the user (the body motion score) may be determined as "0".

When the FMCW scheme as shown in FIG. 8 is employed, intensity of the signal (that is, magnitude of motion) at each distance is calculated, a peak present in the relation between the calculated distance and magnitude of motion is sensed, and the body motion score is determined based on magnitude of motion at that peak.

(c3: First Distance Measurement Unit 2703 and Second Distance Measurement Unit 2705)

Sleep alarm apparatus 2 according to the present embodiment may be configured to measure a distance to a user who is a measurement target, based on an output from Doppler sensor 30. At least one of two types of measurement methods by making use of magnitude of motion as will be described below can be adopted as such a method of measuring a distance to a user.

More specifically, at least one of a method (first distance measurement unit 2703) of measuring a distance with body motion of a user being focused on and a method (sensing result accumulator 2704 and second distance measurement unit 2705) of measuring a distance with breathing by a user being focused on can be adopted. In other words, at least one of first distance measurement unit 2703 and second distance measurement unit 2705 corresponds to the distance measurement unit that measures a distance to the user based on the output from Doppler sensor 30.

(i) First Distance Measurement Unit 2703

As shown in FIG. 8, first distance measurement unit 2703 specifies a peak that appears in a result of sensing (distance-motion information) representing relation between a distance and motion provided from Fourier transformer 2701 as a distance at which body motion of the user is sensed, and provides that distance as the distance to the user (which is denoted as a "distance (a distance based on sensing of body motion)" in FIG. 6).

By measuring a distance with such body motion of the user being focused on, a distance can be measured quickly and highly accurately.

(ii) Sensing Result Accumulator 2704 and Second Distance Measurement Unit 2705

Second distance measurement unit 2705 measures a distance with slight motion such as breathing by the user being focused on. Since a component of motion produced by breathing by the user is normally relatively small, it is difficult to measure the component for each frame. Then, second distance measurement unit 2705 achieves improved measurement accuracy by using a result of sensing (distance-motion information) over a plurality of frames.

Figure 9:
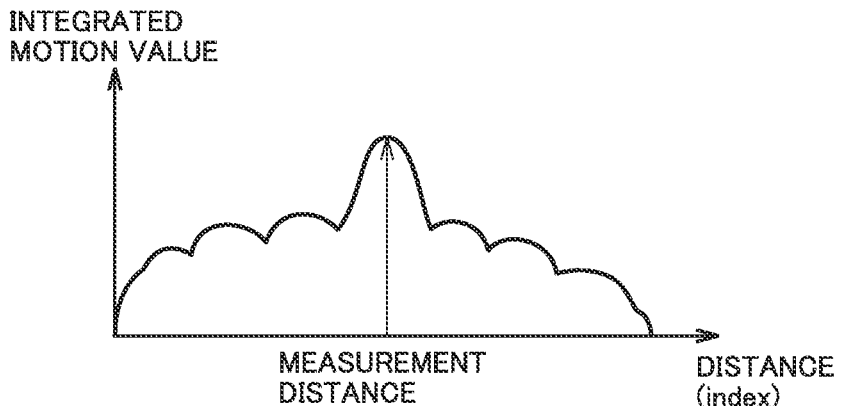
FIG. 9 is a diagram for illustrating a method of measuring a distance with breathing by a user being focused on, in the sleep alarm apparatus according to the present embodiment.

FIG. 9 is a diagram for illustrating a method of measuring a distance with breathing by a user being focused on, in sleep alarm apparatus 2 according to the present embodiment. Referring to FIG. 9, by integrating for each distance, a result of sensing (distance-motion information) obtained during each prescribed period, an integrated result of sensing can be calculated. For example, results of sensing obtained during a prescribed period that lasts for several seconds to more than ten seconds may be integrated.

Then, by referring to the calculated integrated result of sensing, a peak at which magnitude of an integrated motion value is maximum may be specified, and a distance corresponding to the specified peak may be provided as the measured distance (the distance based on sensing of breath). Alternatively, magnitude of the specified peak may be provided as a value representing slight motion.

More specifically, sensing result accumulator 2704 accumulates a result of sensing for each frame over a prescribed period. By implementing sensing result accumulator 2704, for example, with a ring buffer, it can hold a result of sensing in each frame only for a period during which the result of sensing should be accumulated, and can automatically erase the result of sensing for each frame by subsequently overwriting the result of sensing with a new result of sensing. Second distance measurement unit 2705 obtains a graph of an integrated motion value as in FIG. 9, by integrating for each distance, magnitude of motion based on results of sensing over the prescribed period accumulated in sensing result accumulator 2704. Then, a value of a distance (index) corresponding to the peak of the integrated motion value is adopted as the distance (the distance based on sensing of breath).

By using such an integrated result of sensing obtained by integrating the results of sensing over a plurality of frames, even in a situation that body motion is less, the distance to the user can accurately be measured. In other words, even slight motion of the user can be measured.

(c4: Presence Determination Unit 2706)

Sleep alarm apparatus 2 according to the present embodiment may be configured to determine whether or not a user is present within a measurement area based on an output from Doppler sensor 30. Presence determination unit 2706 calculates a "presence score" as an indicator for determining whether or not a user is present within the measurement area. Presence determination unit 2706 determines whether or not a user is present based on a measurement result (an integrated result of sensing) from second distance measurement unit 2705.

The presence score refers to an indicator that indicates a probability of presence of a user within a measurement area based on calculation of magnitude of motion within the measurement area (or within an effective measurement area set in advance or an effective measurement area arbitrarily set by a user) based on an output from Doppler sensor 30. For example, the presence score may be provided as a value normalized to be within a range including a decimal between 0 and 1.

Sleep alarm apparatus 2 according to the present embodiment makes use of a new finding that, in an environment where a user is not present, a characteristic waveform appears in a graph of an integrated result of sensing calculated by second distance measurement unit 2705.

Figure 10:
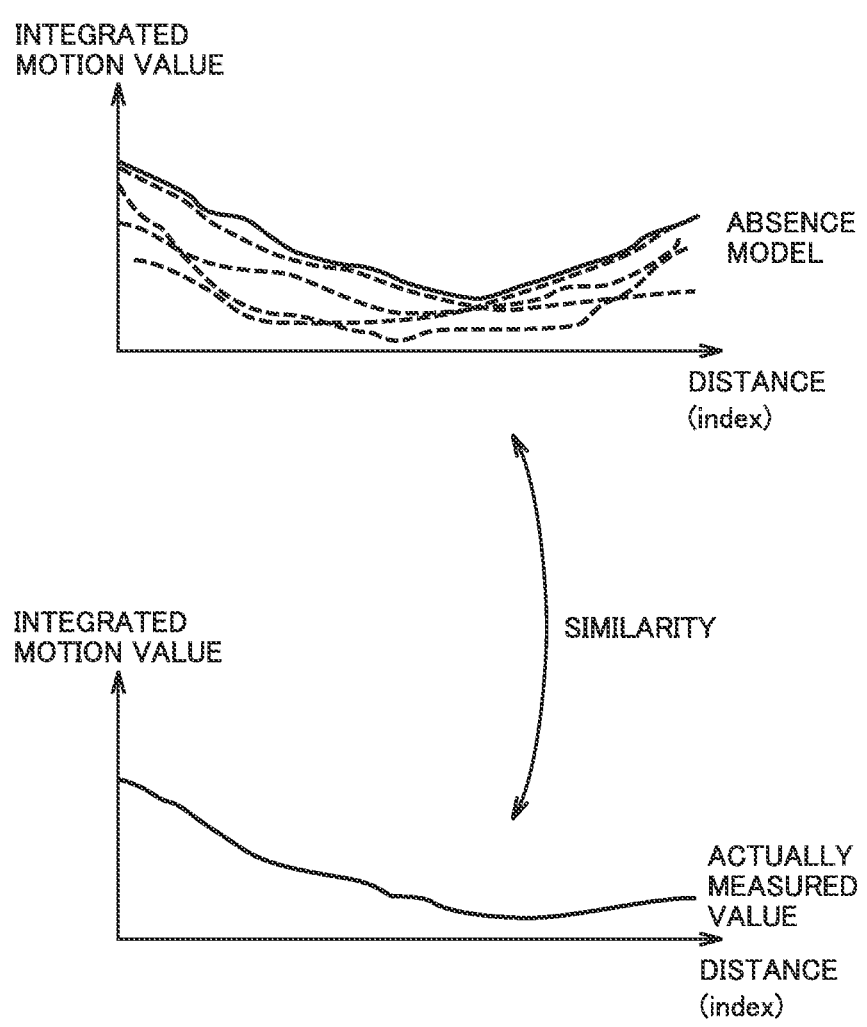
FIG. 10 is a diagram for illustrating a method of calculating a presence score in the sleep alarm apparatus according to the present embodiment.

FIG. 10 is a diagram for illustrating a method of calculating a presence score in sleep alarm apparatus 2 according to the present embodiment. Referring to FIG. 10, in some bedrooms different in size, shape, or the like, actual measurement is conducted while no user is present, and an integrated result of sensing in each environment is calculated. For a graph of each calculated integrated result of sensing, an absence model is determined in advance by adopting for each distance a largest integrated motion value among the integrated motion values shown in each graph and preparing a graph including each adopted value.

By comparing the absence model thus prepared with the integrated result of sensing obtained in actual measurement and evaluating similarity between their shapes, the presence score is calculated. Similarity may be calculated by normalizing each of the absence model and the integrated result of sensing.

When the design such that the presence score exhibits a larger value as possibility of presence of the user within the measurement area is higher is adopted, the presence score exhibits a smaller value as similarity between the absence model and the integrated result of sensing is higher.

Therefore, when the similarity and the presence score are both normalized to be within a range including a decimal between 0 and 1, the presence score can be calculated as the presence score=(1−similarity).

Though an example in which the presence score is calculated based on similarity in shape to the absence model is given in the description above, instead of such a method of determining similarity, the presence score may be high when the integrated result of sensing obtained in actual measurement is equal to or smaller than a value in the absence model at a large number of positions (index).

An example in which a user other than a user who is a measurement target is present within the measurement area is also assumed. In this case, measurement for the user other than the user who is the measurement target is conducted. Then, an effective measurement area may be set in order to focus only on a specific user as a measurement target. In this case, the effective measurement area corresponds to a user-lying area set as an area where a user will lie during sleep, and it is smaller than the measurement area within which a distance can be measured.

Setting acceptor 2707 accepts from a user, setting of the effective measurement area in accordance with an input from a user through input device 29 or microphone 28. Though a default effective measurement area may be set in advance, the effective measurement area may arbitrarily be set or modified by means of setting acceptor 2707.

Presence determination unit 2706 determines a user state as absence when the distance (the distance based on sensing of breath) measured by second distance measurement unit 2705 indicates being out of the effective measurement area.

Normally, the effective measurement area is set within a prescribed distance (for example, 100 cm) from sleep alarm apparatus 2. When the measured distance to the user exceeds this distance, the presence score is fixed to "0". Only one or both of an upper limit and a lower limit of the distance from sleep alarm apparatus 2 may be defined for the effective measurement area. An example in which the upper limit of the distance from sleep alarm apparatus 2 is set is basically described below.

Figure 11A:
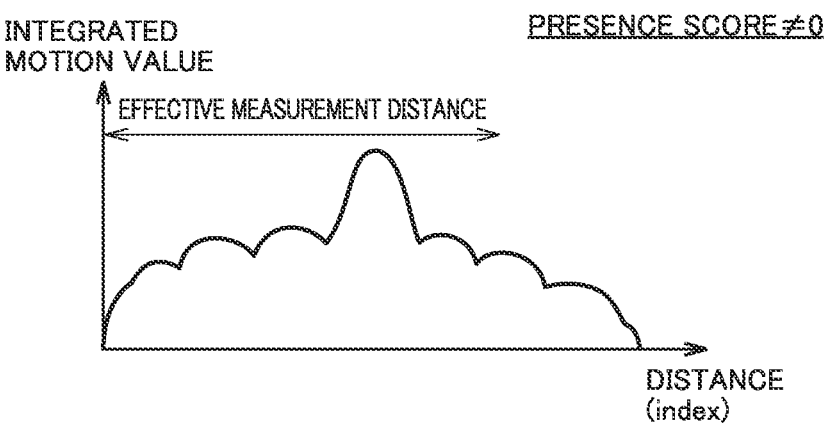
FIGS. 11A and 11B are diagrams for illustrating relation between an effective measurement area and a presence score in the sleep alarm apparatus according to the present embodiment.
Figure 11B:
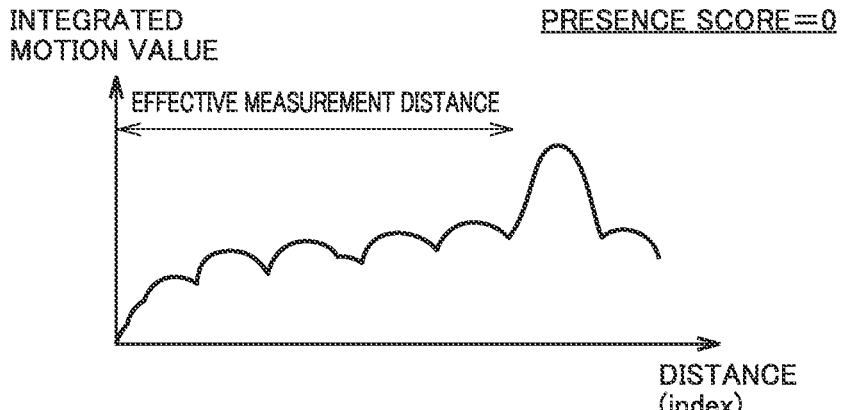

FIGS. 11A and 11B are diagrams for illustrating relation between the effective measurement area and the presence score in sleep alarm apparatus 2 according to the present embodiment. FIG. 11A shows an example in which a position (index) of a peak that appears in an integrated result of sensing is present within the effective measurement area. In the example shown in FIG. 11A, the presence score exhibits some value ($\neq 0$) which represents possibility of presence of a user.

In contrast, FIG. 11B shows an example in which a position (index) of a peak that appears in an integrated result of sensing is present out of the effective measurement area. In the example shown in FIG. 11B, though possibility of presence of the user within the measurement area is high, the user can be determined as not being present within the effective measurement area, and hence the presence score is fixed to "0". In other words, presence determination unit 2706 determines the user as not being present unless the measured distance (the distance (the distance based on sensing of breath)) to the user is within the effective measurement area.

By setting such an effective measurement area, for example, in an example where a user who is the measurement target and a user who is not the measurement target sleep within the measurable area of sleep alarm apparatus 2, such a situation that the user who is the measurement target gets up earlier and measurement for the remaining user who is not the measurement target is continued to consequently provide an incorrect measurement result can be avoided.

(c5: Sleep State Measurement Unit 2708)

Sleep alarm apparatus 2 according to the present embodiment may be configured to measure in real time, a sleep state of a user based on an output from Doppler sensor 30. More specifically, sleep state measurement unit 2708 (FIG. 6) measures in real time, a sleep state of a user based on an output from the sensing unit that outputs a signal depending on motion of the user. In the present embodiment, sleep state measurement unit 2708 measures the sleep state of the user by making use of a sensing signal provided from Doppler sensor 30 representing one example of the sensing unit.

The sleep state of the user may include, for example, five types of absence, wake/presence, light sleep, deep sleep, and REM sleep. The sleep state may be categorized into a smaller or larger number of types.

Typically, sleep state measurement unit 2708 may be implemented by using a trained model created in advance by using a machine learning approach. In this case, incident waves are emitted from Doppler sensor 30 to any subject to obtain a sensing signal (or a result of sensing obtained by Fourier transform of the sensing signal), and in parallel, measurement for the subject with a known approach is conducted to obtain a value representing the sleep state. By tagging the value representing the sleep state corresponding to the sensing signal or the result of sensing, the trained model can be generated, and by using the generated trained model, a trained model can be generated with a known approach.

By using the trained model created with such an arbitrary method, sleep state measurement unit 2708 that measures in real time the sleep state of the user based on an output from Doppler sensor 30 can be implemented.

In successive measurement (real-time measurement) of the sleep state by sleep state measurement unit 2708, some or all of sensing signals from start of sleep until immediately before are used. In other words, in successive measurement of the sleep state, some or all of data in the past until immediately before are referred to.

The sleep state can also subsequently be measured by means of sleep state measurement unit 2708 (post-process measurement). In this case, sensing signals measured before and after time at which a certain sleep state is to be measured can be used. In order to enhance accuracy in measurement of the sleep state, all or some of sensing signals from start of sleep of a user until wake may be used.

In order to hold sensing signals over a certain period, sleep state measurement unit 2708 may be provided with a data accumulator 2712. Data accumulator 2712 of sleep state measurement unit 2708 is preferably configured to hold sensing signals over a period from start of sleep of the user until wake. Thus, in post-process measurement, sleep state measurement unit 2708 calculates, based on data obtained by accumulation of outputs at least during a measurement period from start of sleep until wake of the user, the sleep state during the measurement period. The calculated sleep state may be provided as chronological data over the entirety or a part of the measurement period from start of sleep until wake. This post-process measurement may be conducted by a processing unit different from sleep state measurement unit 2708.

Though FIG. 6 illustrates a configuration in which a result of sensing (distance-motion information) provided from Fourier transformer 2701 is provided to sleep state measurement unit 2708, without being limited as such, the sensing signal from Doppler sensor 30 may directly be provided to sleep state measurement unit 2708.

The presence score calculated by presence determination unit 2706 is provided to sleep state measurement unit 2708. The presence score refers to an indicator for determining whether or not the user is present within the measurement area (or the effective measurement area). When a value of the presence score is smaller than a threshold value (for example, 0.05) set in advance, "absence" may forcibly be provided as the sleep state. As described above, presence determination unit 2706 provides an effective presence score only when the user is present within the effective measurement area, based on the distance measured by second distance measurement unit 2705. By making use of such a presence score, sleep state measurement unit 2708 can measure the sleep state, with the user present within the effective measurement area smaller than the measurement area within which second distance measurement unit 2705 can conduct measurement being focused on, based on a measurement result from second distance measurement unit 2705. In other words, measurement by mistake of the sleep state of a user who is present out of the effective measurement area can be prevented.

Though FIG. 6 shows an exemplary configuration in which "absence" is provided as the sleep state when the value of the presence score calculated by presence determination unit 2706 is smaller than a threshold value set in advance, without being limited as such, any configuration capable of measuring the sleep state with the user present within the effective measurement area being focused on may be adopted. For example, only a component within the effective measurement area in the result of sensing (distance-motion information) provided from Fourier transformer 2701 may be made use of to measure the sleep state.

By adopting sleep state measurement unit 2708 as above, the sleep state of the user can be measured in real time with Doppler sensor 30.

(c6: User State Measurement Unit 2709)

Sleep alarm apparatus 2 according to the present embodiment may be configured to measure a user state representing at least one of a position and motion of a user based on an output from Doppler sensor 30. This user state is different from the sleep state of the user. The user state may include information on whether the user is moving or non-moving. In other words, the user state may represent that the user is moving or non-moving.

Furthermore, the user state may include information (absence) on whether or not the user is present within the measurable area of the sensing unit including the Doppler sensor. In other words, the user state may represent presence or absence of the user. Consequently, the user state may include, for example, three types of moving, non-moving, and absence.

Typically, user state measurement unit 2709 determines which user state the user is in, based on the presence score and the body motion score.

Figure 12:
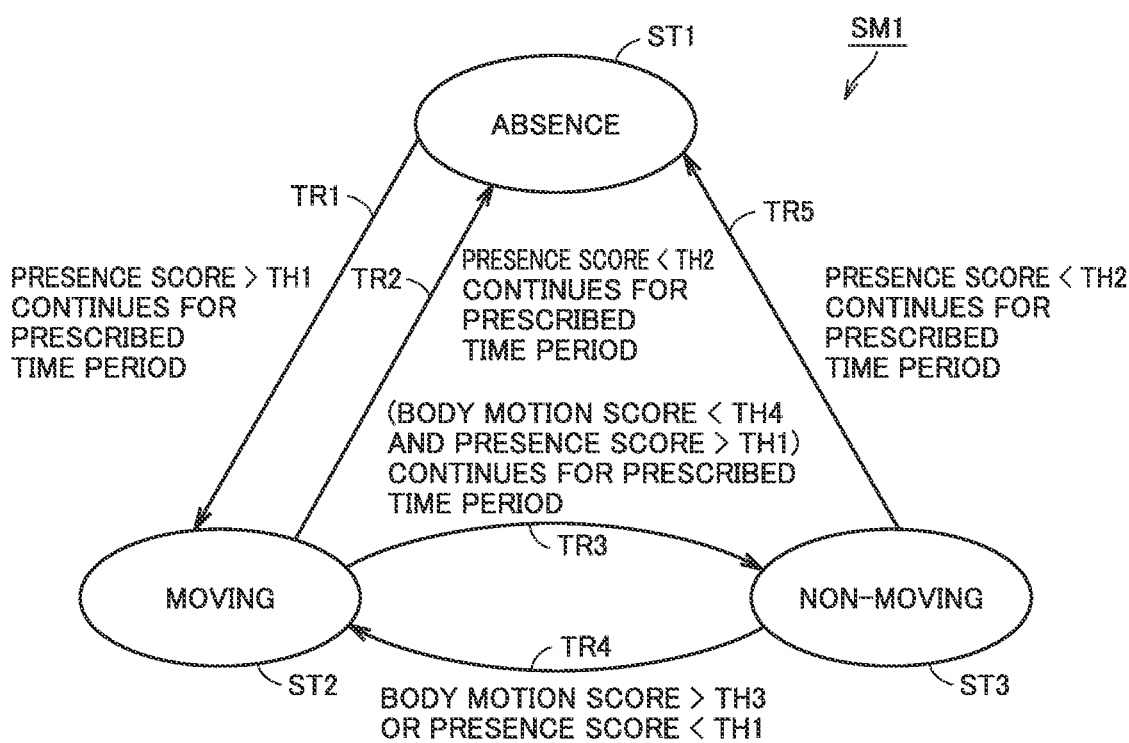
FIG. 12 is a diagram for illustrating a method of measuring a user state in the sleep alarm apparatus according to the present embodiment.

FIG. 12 is a diagram for illustrating a method of measuring a user state in sleep alarm apparatus 2 according to the present embodiment. Referring to FIG. 12, user state measurement unit 2709 holds a state machine SM1 corresponding to each state of the user state. Specifically, state machine SM1 includes an absent state ST1, a moving state ST2, and a non-moving state ST3.

For absent state ST1, transition TR1 to moving state ST2 is defined. For moving state ST2, transition TR2 to absent state ST1 and transition TR3 to non-moving state ST3 are defined. For non-moving state ST3, transition TR4 to moving state ST2 and transition TR5 to absent state ST1 are defined.

Each condition for transition will be described below.

Transition TR1 from absent state ST1 to moving state ST2 is made on condition that the user is present. For example, a state continued for a prescribed period that a value of the presence score exceeds a threshold value TH1 (for example, 0.95) set in advance may be adopted as the transition condition. Threshold value TH1 may be determined based on a range of values of the presence score at which possibility of presence of the user is considered as being sufficiently high.

Transition TR2 from moving state ST2 to absent state ST1 is made on condition that the user is not present. For example, a state continued for a prescribed period that the value of the presence score is smaller than a threshold value TH2 (for example, 0.05) set in advance may be adopted as the transition condition. Threshold value TH2 may be determined based on a range of values of the presence score at which possibility of absence of the user is considered as being sufficiently high.

Transition TR5 from non-moving state ST3 to absent state ST1 may also be made under a condition similar to that for transition TR2.

As described above, when the effective measurement area is set and when no motion of the user is sensed within the effective measurement area, the presence score is fixed to "0" and hence transition to absent state ST1 is made. Therefore, the user state measurement unit measures as the user state, whether or not the user is present (that is, "absence" or otherwise) within the effective measurement area which is the user-lying area set as the area where the user will lie during sleep.

Transition TR3 from moving state ST2 to non-moving state ST3 is made on condition that body motion of the user is relatively small. For example, a state continued for a prescribed period that a value of the body motion score is smaller than a threshold value TH4 and the value of the presence score exceeds threshold value TH1 may be adopted as the transition condition. Threshold value TH4 may be determined based on a range of values of the body motion score at which body motion of the user is considered as being sufficiently small.

Transition TR4 from non-moving state ST3 to moving state ST2 is made on condition that body motion of the user is relatively large. For example, the value of the body motion score exceeding a threshold value TH3 or the value of the presence score being smaller than threshold value TH1 may be adopted as the transition condition. Threshold value TH3 may be determined based on a range of values of the body motion score at which body motion of the user is considered as being sufficiently large.

As set forth above, user state measurement unit 2709 successively makes determination as to the transition condition in accordance with each state to determine which of the three states the state falls under.

Instead of implementing state machine SM1 itself as shown in FIG. 12, such a form of implementation as successively updating a state flag based on each transition condition may be adopted.

Since both of sleep state measurement unit 2708 and user state measurement unit 2709 provide a state "absence", information from one or both of them may selectively be used depending on a situation.

(c7: Sleep State Accumulator 2710 and Sleep Analyzer 2711)

Sleep state accumulator 2710 accumulates the sleep state measured by sleep state measurement unit 2708 over a prescribed period (for example, from start of sleep until getting up). In addition to the sleep state measured by sleep state measurement unit 2708, relevant information may also be accumulated.

Sleep analyzer 2711 analyzes the sleep state accumulated in sleep state accumulator 2710 and relevant information. Sleep analyzer 2711 calculates, for example, a sleep sufficiency degree of the user who is sleeping.

(c8: Processing Performing Unit 2720)

Sleep alarm apparatus 2 according to the present embodiment uses various types of information obtained in processing as described above to perform various types of processing as will be described later. Processing performing unit 2720 performs various types of processing as will be described later, based on at least one of the sleep state of the user measured by sleep state measurement unit 2708 and the user state measured by user state measurement unit 2709. In performing various types of processing as will be described later, processing performing unit 2720 may make use of both of the sleep state of the user measured by sleep state measurement unit 2708 and the user state measured by user state measurement unit 2709. Furthermore, in performing various types of processing, processing performing unit 2720 may make use of the distance measured with body motion of the user being focused on, the distance measured with breathing by the user being focused on, the body motion score, the presence score, a result of analysis of sleep, and the like.

As shown in FIG. 6, sleep state measurement unit 2708 and user state measurement unit 2709 can conduct measurement in parallel in response to an output from the sensing unit that outputs a signal depending on motion of the user, and processing performing unit 2720 can perform processing by making use of each measurement result (the sleep state of the user and the user state).

As processing performing unit 2720 performs various types of processing, display 21, speaker 22, communication device 24, LED 25, and the like may be driven.

Figure 13:
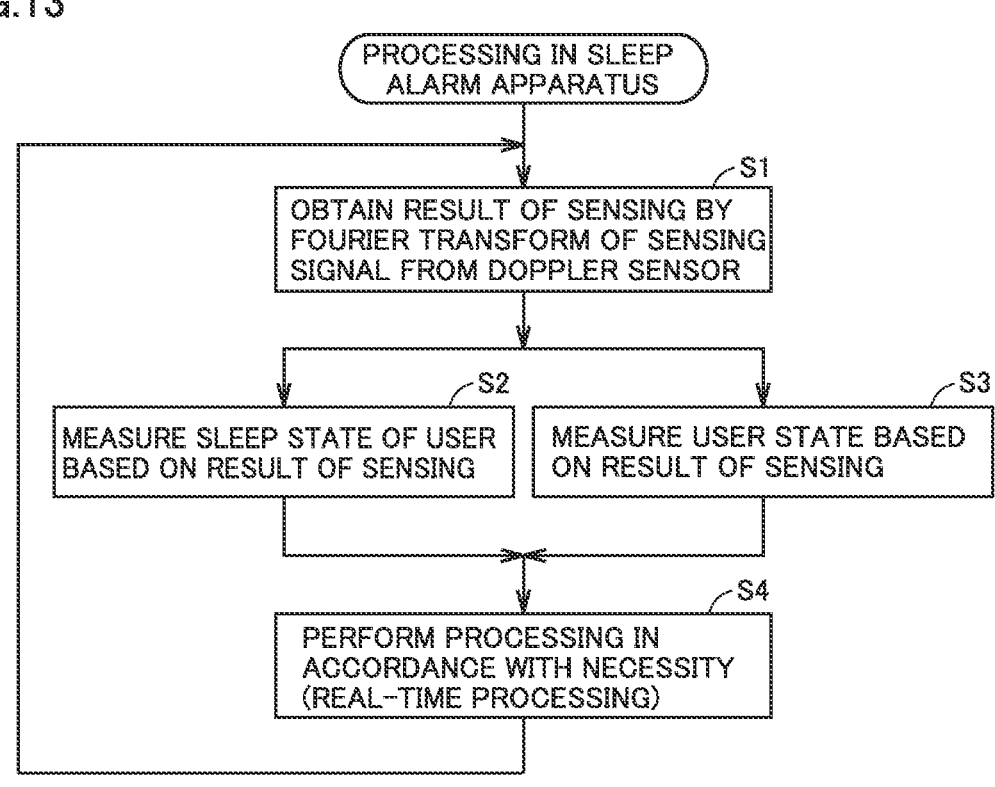
FIG. 13 is a flowchart showing overview of processing performed by the sleep alarm apparatus according to the present embodiment.

FIG. 13 is a flowchart showing overview of processing performed by sleep alarm apparatus 2 according to the present embodiment. Each step shown in FIG. 13 is typically implemented by execution by CPU 27 of sleep alarm apparatus 2, of processing program 231 stored in memory 23.

Referring to FIG. 13, sleep alarm apparatus 2 obtains by Fourier transform of a sensing signal from Doppler sensor 30, a result of sensing (distance-motion information) showing relation between the distance and motion (step S1).

In succession, sleep alarm apparatus 2 measures the sleep state of the user based on the obtained result of sensing (distance-motion information) (step S2) and measures the user state based on the obtained result of sensing (distance-motion information) (step S3).

Then, sleep alarm apparatus 2 performs processing in accordance with necessity (real-time processing) based on the sleep state of the user measured in step S2 and the user state measured in step S3 (step S4).

A series of processing shown in FIG. 13 is repeatedly performed while sleep alarm apparatus 2 is set to be active.

As described above, processing performed by processing performing unit 2720 of sleep alarm apparatus 2 according to the present embodiment is real-time processing successively performed based on the sleep state successively measured by sleep state measurement unit 2708 and/or the user state successively measured by user state measurement unit 2709. In other words, processing performing unit 2720 performs the real-time processing based on the sleep state successively measured by sleep state measurement unit 2708. As will be described later, the real-time processing may be performed to control an alarm.

In a typical example of such control of an alarm, processing for activating audio alarm from speaker 22 or the like when a condition set and determined in advance is satisfied for getting the user up may be included. Processing performing unit 2720 of sleep alarm apparatus 2 thus performs various types of processing including processing relating to the audio alarm for the user. Real-time processing may thus be performed to control audio output.

Sleep alarm apparatus 2 according to the present embodiment may execute, as a mode for activating an audio alarm, (1) a mode on condition that alarm set time set in advance comes (which is also referred to as a "time alarm mode" below) and (2) a mode on condition that the user has slept for a predetermined period or longer (which is also referred to as a "sleep sufficiency mode" below).

An alarm function of sleep alarm apparatus 2 for waking a user up will mainly be described below.

D. Time Alarm Mode

In the time alarm mode, when time set in advance (alarm set time) comes, sleep alarm apparatus 2 (processing performing unit 2720) performs processing for activating the audio alarm. Real-time processing thus performed by processing performing unit 2720 of sleep alarm apparatus 2 may include processing for activating the audio alarm when time set in advance comes. Contents of processing performed by sleep alarm apparatus 2 may be different based on at least one of the sleep state of the user and the user state at the alarm set time.

Figure 14:
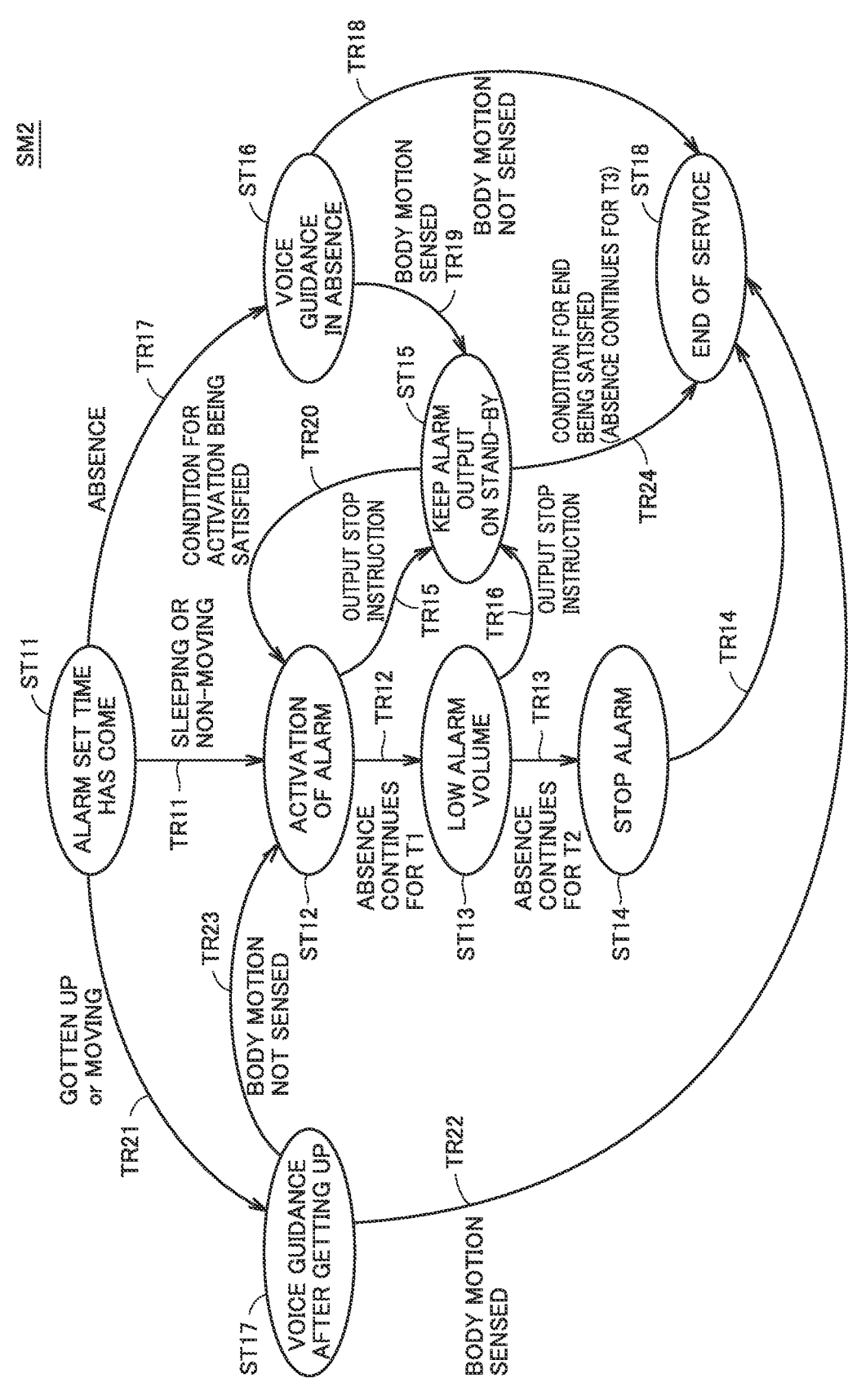
FIG. 14 is a state transition diagram showing an exemplary operation in a time alarm mode of the sleep alarm apparatus according to the present embodiment.

FIG. 14 is a state transition diagram showing an exemplary operation in the time alarm mode of sleep alarm apparatus 2 according to the present embodiment. Referring to FIG. 14, processing performing unit 2720 holds a state machine SM2 corresponding to the time alarm mode.

When the alarm set time comes in state machine SM2, a state ST11 is set. In state ST11, the sleep state of the user and the user state are referred to and transition to any of states ST12, ST16, and ST17 is made.

When the user is sleeping (that is, the sleep state falls under any of "light sleep," "deep sleep," and "REM sleep") or the user state falls under "non-moving" at the alarm set time, transition TR11 from state ST11 to state ST12 is made. The condition for transition to state ST12 intends that the user is sleeping or is not sufficiently awake.

When the user is absent (that is, the sleep state falls under "absence" or the user state falls under "absence") at the alarm set time, transition TR17 from state ST11 to state ST16 is made. The condition for transition to state ST16 intends that the user has already left the bed.

When the user has gotten up (that is, the sleep state falls under "gotten up" or the user state falls under "moving") at the alarm set time, transition TR21 from state ST11 to state ST17 is made. The condition for transition to state ST17 intends that the user is sufficiently awake.

In state ST12, sleep alarm apparatus 2 gives the audio alarm from speaker 22. Output of the audio alarm continues until the condition for transition to state ST13 or state ST15 is satisfied.

More specifically, in state ST12, when a state that the user is absent (that is, the sleep state falls under "absence" or the user state falls under "absence") continues for a time period T1 or longer, transition TR12 to state ST13 is made. The condition for transition to state ST13 intends a state that possibility of the user having left the bed is high.

In state ST13, sleep alarm apparatus 2 lowers a volume of the audio alarm that is being given (lowering in volume of the alarm). Thus, in response to the determination that a period for which the user is determined as not being present within the user-lying area is equal to or longer than time period T1 (a first prescribed time period) when the audio alarm is ringing, processing performing unit 2720 lowers the volume of the audio alarm that is being given.

In state ST13, when a state that the user is absent (that is, the sleep state falls under "absence" or the user state falls under "absence") continues for a time period T2 or longer, transition TR13 to state ST14 is made. The condition for transition to state ST14 intends a state that the user is confirmed as having left the bed.

In state ST14, sleep alarm apparatus 2 stops the audio alarm that is being given (alarm stop). Thus, in response to the determination that the period for which the user is determined as not being present within the user-lying area is equal to longer than time period T2 (a second prescribed time period) when the audio alarm is ringing, processing performing unit 2720 stops the audio alarm that is being given. After the audio alarm is stopped, transition TR14 to state ST18 is made. In state ST18, a service in the time alarm mode ends. A voice message notifying that the service in the time alarm mode ends may be provided from speaker 22.

When the user gives an output stop instruction in state ST12, transition TR15 to state ST15 is made. Similarly, when the user gives the output stop instruction in state ST13, transition TR16 to state ST15 is made. The condition for transition to state ST15 means an instruction by the user to once stop the audio alarm and to provide output again after a prescribed time period. In state ST15, sleep alarm apparatus 2 keeps output of the audio alarm on stand-by.

When a predetermined output condition is satisfied in state ST15 (for example, lapse of a prescribed time period since transition to state ST15), transition TR20 to state ST12 is made. In state ST12, sleep alarm apparatus 2 gives or gives again the audio alarm.

When a predetermined quitting condition is satisfied in state ST15 (for example, a state of absence of the user continues for a time period T3 or longer), transition TR24 to state ST18 is made. In state ST18, the service in the time alarm mode ends.

In state ST16, sleep alarm apparatus 2 provides from speaker 22, a voice message on the premise that the user is absent (voice guidance in absence). The voice message corresponding to the voice guidance in absence may be, for example, "Since you are not around here, the audio alarm ends. If you do not want the end, please give a cue, for example, by moving your body." Thus, in response to the determination that the user is not present within the user-lying area at the time when time set in advance comes, processing performing unit 2720 provides the voice message (a first voice message) on the premise that the user is absent, instead of the audio alarm.

In state ST16, whether or not there is body motion of the user after output of the voice message is determined. When body motion of the user is not sensed in state ST16, transition TR18 to state ST18 is made. In state ST18, the service in the time alarm mode ends. The condition for transition to state ST18 intends that the user has already left the bed and output of the audio alarm is not necessary. Thus, when body motion sensing unit 2702 does not sense body motion of the user during a stand-by time period after output of the voice message (first voice message) on the premise that the user is absent, processing performing unit 2720 quits performing the series of processing.

When body motion of the user is sensed in state ST16, transition TR19 to state ST15 is made. In state ST15, sleep alarm apparatus 2 keeps output of the audio alarm on stand-by. The condition for transition to state ST15 intends that, though the user is determined as having left the bed, output again of the audio alarm is necessary in consideration of possibility that such determination was made due to erroneous sensing. Thus, in response to sensing, by body motion sensing unit 2702, of body motion of the user after output of the voice message (first voice message) on the premise that the user is absent, processing performing unit 2720 postpones activation of the audio alarm.

In state ST17, sleep alarm apparatus 2 provides from speaker 22, a voice message on the premise that the user has already waken up (voice guidance after getting-up). The voice message corresponding to the voice guidance after getting-up may be, for example, "You seem to have already waken up. If you want the end of the audio alarm, please give a cue, for example, by moving your body." Thus, in response to the determining, by sleep state measurement unit 2708, that the user has gotten up at the time when time set in advance comes, processing performing unit 2720 provides a voice message (second voice message) on the premise that the user has already waken up, instead of the audio alarm.

In state ST17, whether or not there is body motion of the user after output of the voice message is determined. When body motion of the user is sensed in state ST17, transition TR22 to state ST18 is made. In state ST18, the service in the time alarm mode ends. The condition for transition to state ST18 intends that the user has already waken up and output of the audio alarm is not necessary. Thus, in response to sensing by body motion sensing unit 2702, of body motion of the user after output of the voice message (second voice message) on the premise that the user has already waken up, processing performing unit 2720 quits processing for activating the audio alarm.

When body motion of the user is not sensed in state ST17, transition TR19 to state ST12 is made. In state ST12, sleep alarm apparatus 2 gives the audio alarm from speaker 22. The condition for transition to state ST12 intends a state that wake of the user is not sufficient. Thus, in response to the determination that body motion sensing unit 2702 does not sense body motion of the user after output of the voice message (second voice message) on the premise that the user has already waken up, processing performing unit 2720 activates the audio alarm.

Instead of implementing state machine SM2 itself as shown in FIG. 14, such a form of implementation as successively updating a state flag based on each transition condition may be adopted. Only some of states included in state machine SM2 shown in FIG. 14 may be implemented or another state may further be added.

Figure 15:
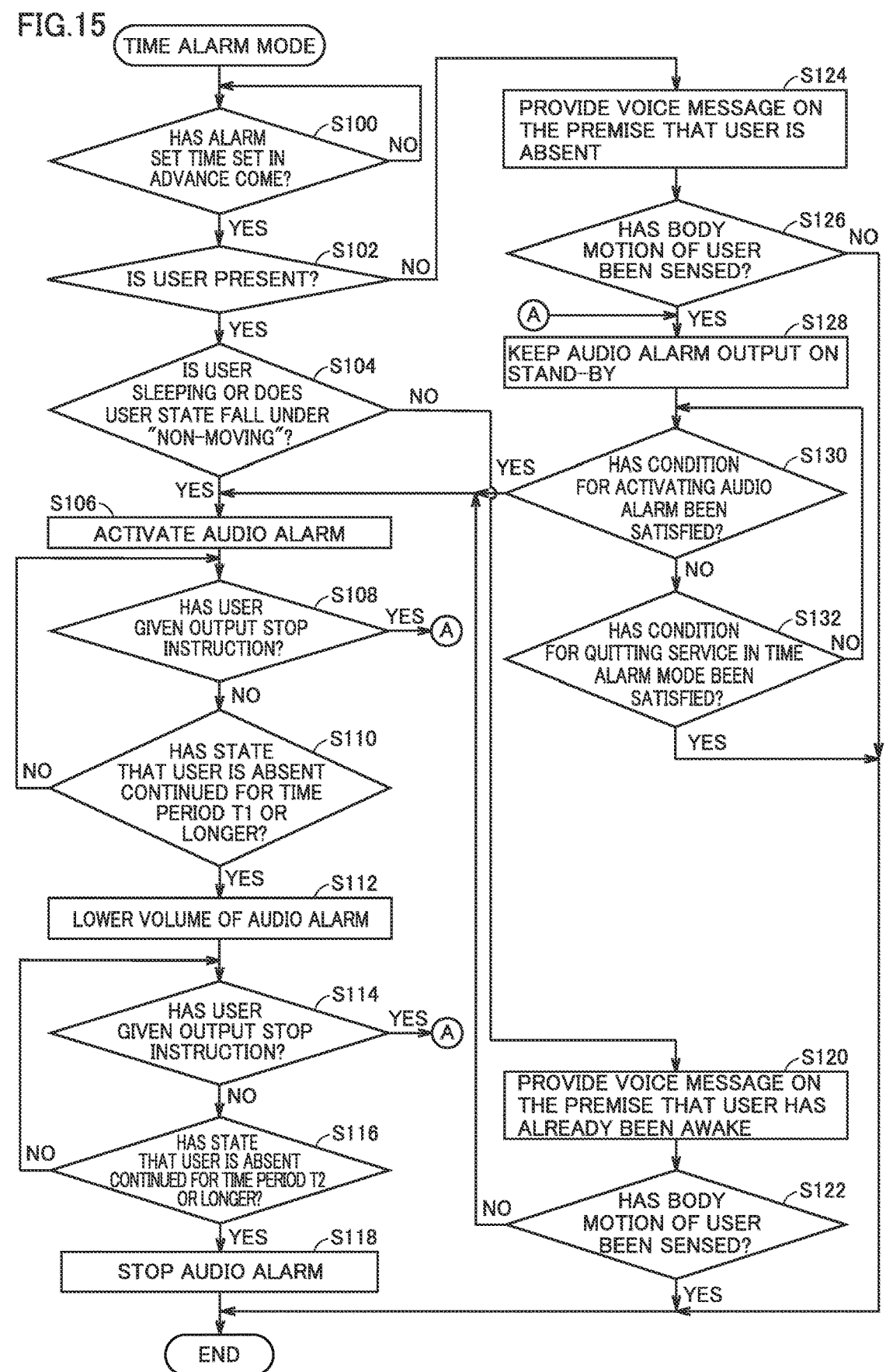
FIG. 15 is a flowchart showing a processing procedure in the time alarm mode of the sleep alarm apparatus according to the present embodiment.

FIG. 15 is a flowchart showing a processing procedure in the time alarm mode of sleep alarm apparatus 2 according to the present embodiment. Each step shown in FIG. 15 is typically implemented by execution by CPU 27 of sleep alarm apparatus 2, of processing program 231 stored in memory 23.

Referring to FIG. 15, sleep alarm apparatus 2 determines whether or not alarm set time set in advance has come (step S100). When the alarm set time set in advance has not yet come (NO in step S100), processing in step S100 is repeated.

When the alarm set time set in advance has come (YES in step S100), sleep alarm apparatus 2 determines whether or not the user is present (step S102).

When the user is present (YES in step S102), sleep alarm apparatus 2 determines whether or not the user is sleeping or the user state falls under "non-moving" (step S104).

When the user is sleeping or the user state falls under "non-moving" (YES in step S104), sleep alarm apparatus 2 activates the audio alarm (step S106). Then, sleep alarm apparatus 2 determines whether or not the user has given the output stop instruction (step S108). When the user has given the output stop instruction (YES in step S108), the process proceeds to step S128.

When the user has not given the output stop instruction (NO in step S108), sleep alarm apparatus 2 determines whether or not a state that the user is absent has continued for time period T1 or longer (step S110). When the state that the user is absent has not continued for time period T1 or longer (NO in step S110), processing in step S108 or later is repeated.

When the state that the user is absent has continued for time period T1 or longer (YES in step S110), sleep alarm apparatus 2 lowers the volume of the audio alarm that is being given (step S112). Then, sleep alarm apparatus 2 determines whether or not the user has given the output stop instruction (step S114). When the user has given the output stop instruction (YES in step S114), the process proceeds to step S128.

When the user has not given the output stop instruction (NO in step S114), sleep alarm apparatus 2 determines whether or not the state that the user is absent has continued for time period T2 or longer (step S116). When the state that the user is absent has not continued for time period T2 or longer (NO in step S116), processing in step S114 or later is repeated.

When the state that the user is absent has continued for time period T2 or longer (YES in step S116), sleep alarm apparatus 2 stops the audio alarm that is being given (step S118). Then, the process ends.

When the user is not sleeping and the user state does not fall under "non-moving" (NO in step S104), sleep alarm apparatus 2 determines the user as having gotten up and provides from speaker 22, the voice message (voice guidance after getting-up) on the premise that the user has already waken up (step S120). Then, sleep alarm apparatus 2 determines whether or not body motion of the user has been sensed (step S122).

When body motion of the user has been sensed (YES in step S122), sleep alarm apparatus 2 quits the process without activating the audio alarm. In contrast, when body motion of the user has not been sensed (NO in step S122), processing in step S106 or later is performed.

When the user is not present (NO in step S102), sleep alarm apparatus 2 provides from speaker 22, the voice message (voice guidance in absence) on the premise that the user is absent (step S124). Then, sleep alarm apparatus 2 determines whether or not body motion of the user has been sensed (step S126).

When body motion of the user has not been sensed (NO in step S126), the process ends without activating the audio alarm. In contrast, when body motion of the user has been sensed (YES in step S126), sleep alarm apparatus 2 keeps output of the audio alarm on stand-by (step S128). Then, sleep alarm apparatus 2 determines whether or not a condition for activating the audio alarm has been satisfied (step S130). When the condition for activating the audio alarm has been satisfied (YES in step S130), processing in step S106 is performed.

In contrast, when the condition for activating the audio alarm has not been satisfied (NO in step S130), sleep alarm apparatus 2 determines whether or not a condition for quitting the service in the time alarm mode has been satisfied (step S132). When the condition for quitting the service in the time alarm mode has been satisfied (YES in step S132), sleep alarm apparatus 2 quits the process. When the condition for quitting the service in the time alarm mode has not been satisfied (NO in step S132), processing in step S130 or later is repeated.

Through processing as above, the time alarm mode can be implemented.

E. Sleep Sufficiency Mode

In a sleep sufficiency mode, when the user is determined as having slept for an amount equal to or larger than a predetermined amount, sleep alarm apparatus 2 (processing performing unit 2720) activates the audio alarm. In the sleep sufficiency mode, typically, a sleep sufficiency degree of a user who is sleeping that is calculated by sleep analyzer 2711 (FIG. 6) is used.

Sleep analyzer 2711 determines whether or not the user has sufficiently slept by successively calculating a score based on the sleep state accumulated in sleep state accumulator 2710 over a prescribed period (for example, from start of sleep until getting up). For example, the sleep sufficiency degree is designed to be larger in value as a time period of deep sleep provided as the sleep state is longer and to be larger in value as the number of times of wake is smaller.

Thus, processing performing unit 2720 determines whether or not the user has slept for the predetermined amount or larger based on the score calculated by sleep analyzer 2711 based on a result of measurement.

Figure 16:
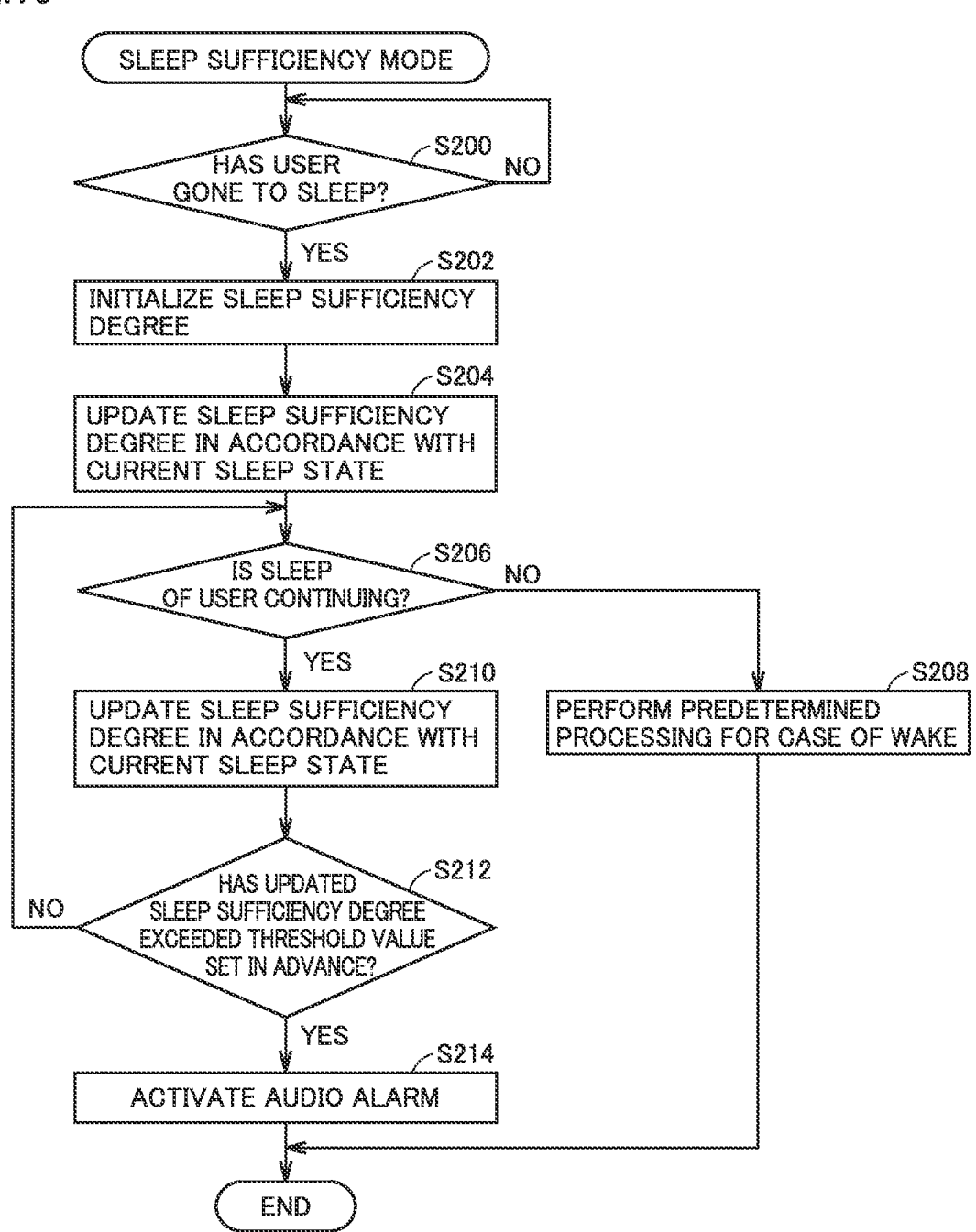
FIG. 16 is a flowchart showing a processing procedure in a sleep sufficiency mode of the sleep alarm apparatus according to the present embodiment.

FIG. 16 is a flowchart showing a processing procedure in the sleep sufficiency mode of sleep alarm apparatus 2 according to the present embodiment. Each step shown in FIG. 16 is typically implemented by execution by CPU 27 of sleep alarm apparatus 2, of processing program 231 stored in memory 23.

Referring to FIG. 16, sleep alarm apparatus 2 determines whether or not the user has gone to sleep (step S200). In step S200, the user who has gone to sleep means that the measured sleep state falls under any of "light sleep," "deep sleep," and "REM sleep." When the user has not gone to sleep (NO in step S200), processing in step S200 is repeated.

When the user has gone to sleep (YES in step S200), sleep alarm apparatus 2 initializes the sleep sufficiency degree (step S202) and updates the sleep sufficiency degree in accordance with the current sleep state (step S204).

In succession, sleep alarm apparatus 2 determines whether or not sleep of the user is continuing (step S206). When sleep of the user is not continuing (NO in step S206), sleep alarm apparatus 2 performs predetermined processing for a case of wake (step S208). Then, the process ends. When the user has gone to sleep again, processing in step S206 or later may again be performed.

When sleep of the user is continuing (YES in step S206), sleep alarm apparatus 2 updates the sleep sufficiency degree in accordance with the current sleep state (step S210). Then, sleep alarm apparatus 2 determines whether or not the updated sleep sufficiency degree has exceeded a threshold value set in advance (step S212). When the updated sleep sufficiency degree has not exceeded the threshold value set in advance (NO in step S212), processing in step S206 or later is repeated.

When the updated sleep sufficiency degree has exceeded the threshold value set in advance (YES in step S212), sleep alarm apparatus 2 activates the audio alarm (step S214). Then, audio alarm output processing ends. After activation of the audio alarm, processing as in the time alarm mode as shown in FIG. 15 may be performed.

Through processing as above, the sleep sufficiency mode can be implemented.

F. Awakening

As described above, in the time alarm mode, when time set in advance (alarm set time) comes, the audio alarm is activated. Depending on a situation, the user may wake up before such alarm set time comes.

Sleep alarm apparatus 2 according to the present embodiment successively measures the sleep state of the user and the user state. Therefore, sleep alarm apparatus 2 can sense also awakening of the user. At the time of awakening of the user, appropriate processing may be performed based on at least one of the sleep state of the user and the user state. Processing performing unit 2720 may thus perform real-time processing in response to transition of the sleep state to a prescribed state before time set in advance (alarm set time).

For example, at the time of awakening of the user, in order to assist the user to leave the bed, LED 25 of sleep alarm apparatus 2 may be turned on or luminance of the backlight of display 21 may be increased. Furthermore, when the user has gone to sleep again, LED 25 or display 21 may be turned off and monitoring in the time alarm mode may be continued. When the state that the user is absent continues for a prescribed time period or longer, LED 25 or display 21 may be turned off and the service in the time alarm mode may end.

Figure 17:
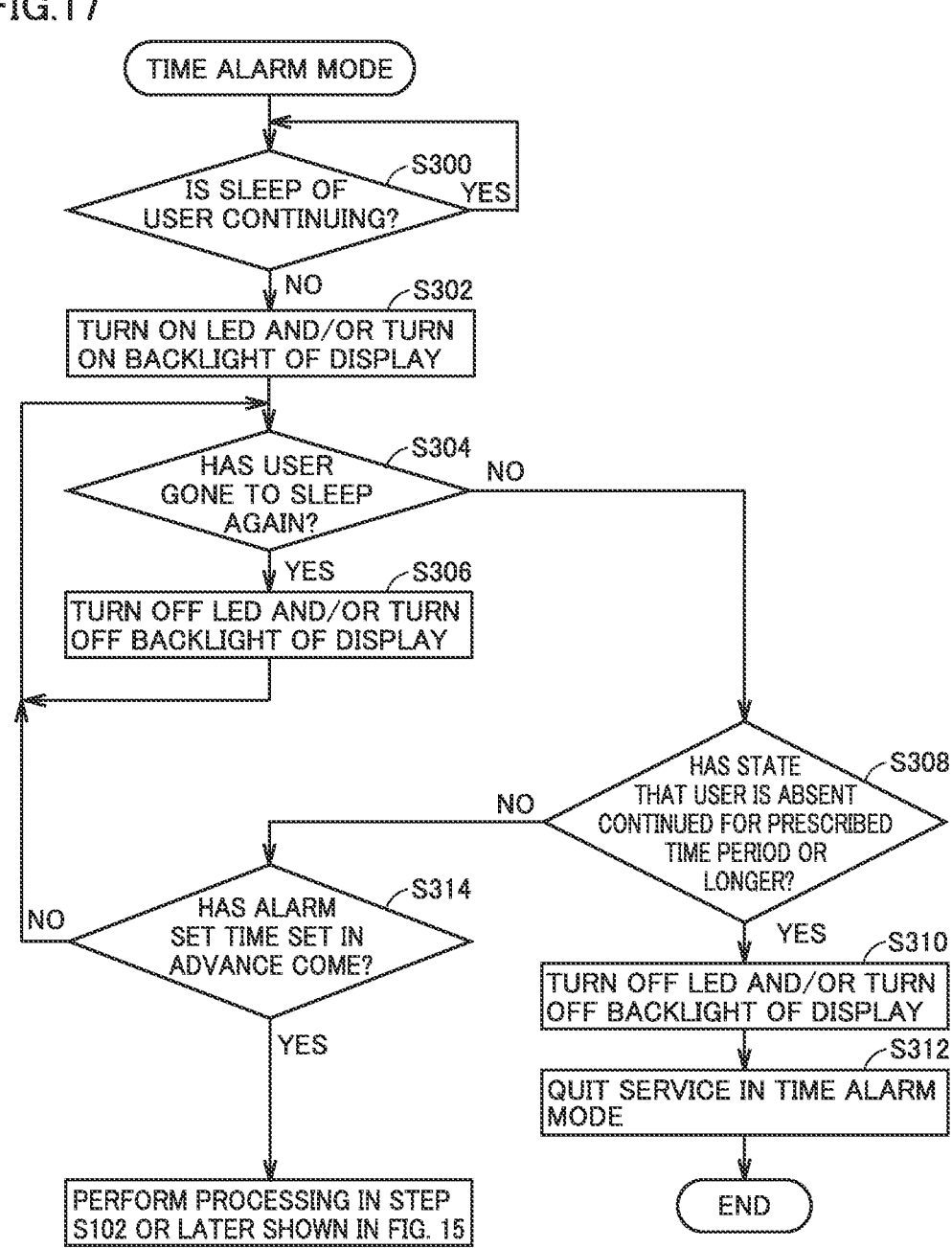
FIG. 17 is a flowchart showing another processing procedure in the time alarm mode of the sleep alarm apparatus according to the present embodiment.

FIG. 17 is a flowchart showing another processing procedure in the time alarm mode of sleep alarm apparatus 2 according to the present embodiment. Each step shown in FIG. 17 is typically implemented by execution by CPU 27 of sleep alarm apparatus 2, of processing program 231 stored in memory 23.

Referring to FIG. 17, sleep alarm apparatus 2 determines whether or not sleep of the user is continuing in the time alarm mode (step S300). Continued sleep of the user in step S300 means that the measured sleep state falls under any of "light sleep," "deep sleep," and "REM sleep." When sleep of the user is continuing (YES in step S300), processing in step S300 is repeated.

When sleep of the user is not continuing (NO in step S300), sleep alarm apparatus 2 turns on LED 25 and/or turns on the backlight of display 21 (step S302).

Then, sleep alarm apparatus 2 determines whether or not the user has gone to sleep again (step S304). When the user is determined as having gone to sleep again (any of light sleep, deep sleep, and REM sleep) (YES in step S304), sleep alarm apparatus 2 turns off LED 25 and/or turns off the backlight of display 21 (step S306), and processing in step S304 or later is repeated.

When the user is determined as not having gone to sleep again (NO in step S304), sleep alarm apparatus 2 determines whether or not the state that the user is absent (a state that the presence score is low) has continued for a prescribed time period or longer (step S308).

When the state that the user is absent is determined as having continued for the prescribed time period or longer (YES in step S308), sleep alarm apparatus 2 turns off LED 25 and/or turns off the backlight of display 21 (step S310), and quits the service in the time alarm mode (step S312).

In contrast, when the state that the user is absent is determined as not having continued for the prescribed time period or longer (NO in step S308), sleep alarm apparatus 2 determines whether or not the alarm set time set in advance has come (step S314). When the alarm set time set in advance has come (YES in step S314), sleep alarm apparatus 2 performs processing in step S102 or later shown in FIG. 15.

When the alarm set time set in advance has not yet come (NO in step S314), processing in step S304 or later is repeated.

Processing in FIG. 17 is repeated until time set in advance (alarm set time) comes. The entirety or a part of processing as shown in FIG. 17 may be performed as predetermined processing for the case of wake in FIG. 16 (step S208).

Through processing as above, processing for addressing awakening of the user can be implemented.

G. Advantages

According to the present embodiment, appropriate processing in accordance with one or both of the sleep state of the user and the user state which is at least one of the position and motion of the user can be performed.

While certain example systems, methods, devices, and apparatuses have been described herein, it is to be understood that the appended claims are not to be limited to the systems, methods, devices, and apparatuses disclosed, but on the contrary, are intended to cover various modifications and equivalent arrangements included within the spirit and scope of the appended claims.

The invention claimed is:

1. An alarm clock comprising:
   a housing;
   a display disposed on or in the housing, the display having a display backlight;
   at least one sensor disposed on or in the housing, the at least one sensor configured to measure distance to a body distinguishing between (a) a wakeful human presence, (b) a sleeping human presence, and (c) no human presence, wherein distinguishing (c) no human presence from (a) a wakeful human presence and/or (b) a sleeping human presence is based on detected change in distance within a distance measurement area in response to an output of the at least one sensor;
   at least one sound transducer disposed on or in the housing; and
   at least one processor disposed in the housing and configured to execute program instructions to perform operations comprising:
      control the display to display a time indication,
      cause the at least one sound transducer to emit an awakening sound in response to body motion detected by the at least one sensor; and
      select and control illumination level of the display backlight based on distinguished no human presence at time of a wake event.

2. The alarm clock of claim 1 wherein no human presence is distinguished when the at least one sensor detects motion within the distance measurement area but substantive motion within an effective distance measurement area is not detected.

3. The alarm clock of claim 1 wherein the illumination level of the display backlight is increased for the at least one sensor distinguishing a wakeful human presence.

4. The alarm clock of claim 1 wherein the illumination level of the display backlight is selected based on the at least one sensor distinguishing no human presence.

5. The alarm clock of claim 1 wherein the sound transducer emission is conditioned on distinguished human presence.

6. The alarm clock of claim 5 wherein the at least one sound transducer is controlled to emit a first sound in response to the wake event when the at least one sensor distinguishes no human presence, and to emit a second sound different from the first sound in response to the wake event when the at least one sensor distinguishes a sleeping human presence.

7. The alarm clock of claim 1 wherein the display backlight is controlled to decrease brightness when the at least one sensor distinguishes a sleeping human presence.

8. The alarm clock of claim 1 wherein the display backlight is controlled to increase brightness when the at least one sensor distinguishes a wakeful human presence.

9. The alarm clock of claim 1 wherein the wake event comprises a prescheduled wake time.

10. The alarm clock of claim 1 wherein the at least one sensor further distinguishes different sleep levels of sleeping human presence.

11. The alarm clock of claim 1 wherein illumination level of the display backlight is changed upon the at least one sensor detecting transition between wakeful human presence and sleeping human presence.

12. The alarm clock of claim 1 wherein the distance of the distance measurement area is settable by a user, and the operation of select and control illumination level of the display backlight comprises select and control the illumination level of the display backlight to be off.

13. An alarm clock comprising:
a housing;
a display disposed on or in the housing, the display having a backlight;
at least one sensor disposed on or in the housing, the at least one sensor configured to measure distance to a body, the at least one sensor providing sensor signals distinguishing between (a) a wakeful human presence, (b) a sleeping human presence, and (c) no human presence, wherein distinguishing (c) no human presence from (a) a wakeful human presence and/or (b) a sleeping human presence is based on detected change in distance within a distance measurement area in response to an output of the at least one sensor; and
at least one processor disposed in the housing and configured to execute program instructions to perform operations comprising:
control the display to display time,
control a sound transducer to emit an awakening sound in response to the sensor signals; and
select and control illumination level of the backlight based on distinguished no human presence at the time of a wake event.

14. The alarm clock of claim 13 wherein the distance of the distance measurement area is settable by a user, and the operation of select and control illumination level of the backlight comprises select and control the illumination level of the backlight to be off.

15. An alarm clock comprising:
a housing;
a display disposed on or in the housing, the display having a backlight;
at least one sensor configured to measure distance to a body, the at least one sensor disposed on or in the housing, the at least one sensor distinguishing between (a) a wakeful human presence, (b) a sleeping human presence, and (c) no human presence, wherein distinguishing (c) no human presence from (a) a wakeful human presence and/or (b) a sleeping human presence is based on detected change in distance within a distance measurement area in response to an output of the at least one sensor; and
processing circuitry disposed in the housing and configured to:
control the display to display a time indication,
control emission of an awakening sound in response to body motion detected by the at least one sensor, and
set illumination level of the backlight based at least in part on the distinguished no human presence at the time of a wake event.

16. The alarm clock of claim 15 wherein the distance of the distance measurement area is settable by a user, and set illumination level of the backlight comprises set the illumination level of the backlight to be off.

17. A method comprising:
controlling a display to display a time indication, the display having a display backlight; using at least one sensor configured to measure distance to a body, the at least one sensor disposed on or in a housing to distinguish between (a) a wakeful human presence, (b) a sleeping human presence, and (c) no human presence, wherein distinguishing (c) no human presence from (a) a wakeful human presence and/or (b) a sleeping human presence is based on detected change in distance within a distance measurement area in response to an output of the at least one sensor;
causing emission of an awakening sound in response to the at least one sensor detecting body motion; and
setting an illumination level of the display backlight based at least in part on the distinguished no human presence at the time of a wake event.

18. The method of claim 17 further including distinguishing no human presence when the at least one sensor detects motion within the distance measurement area but substantive motion within an effective distance measurement area is not detected.

19. The method of claim 17 further including selecting the illumination level of the display backlight based on distinguishing no human presence.

20. The method of claim 17 wherein the distance of the distance measurement area is settable by a user, and setting the illumination level of the display backlight comprises setting the illumination level of the display backlight to be off.

* * * * *